United States Patent
Burke, Jr. et al.

(10) Patent No.: US 7,767,645 B2
(45) Date of Patent: Aug. 3, 2010

(54) SH2 DOMAIN BINDING INHIBITORS

(75) Inventors: Terrence R. Burke, Jr., Bethesda, MD (US); Zhen-Dan Shi, Frederick, MD (US); Sang-Uk Kang, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 281 days.

(21) Appl. No.: 11/932,424

(22) Filed: Oct. 31, 2007

(65) Prior Publication Data

US 2008/0132469 A1 Jun. 5, 2008

Related U.S. Application Data

(63) Continuation of application No. 10/944,699, filed on Sep. 17, 2004, now abandoned.

(60) Provisional application No. 60/504,241, filed on Sep. 18, 2003.

(51) Int. Cl.
*A61K 38/12* (2006.01)
(52) U.S. Cl. ........................................................ 514/11
(58) Field of Classification Search ....................... None
See application file for complete search history.

(56) References Cited

U.S. PATENT DOCUMENTS

| | | |
|---|---|---|
| 3,906,031 A | 9/1975 | Carpino et al. |
| 4,394,519 A | 7/1983 | Carpino et al. |
| 4,879,398 A | 11/1989 | Getman et al. |
| 5,182,263 A | 1/1993 | Danho et al. |
| 5,200,546 A | 4/1993 | Burke, Jr. et al. |
| 5,272,268 A | 12/1993 | Toyoda et al. |
| 5,296,608 A | 3/1994 | Danho et al. |
| 5,369,110 A | 11/1994 | Schmidlin et al. |
| 5,457,114 A | 10/1995 | Stüber et al. |
| 5,463,062 A | 10/1995 | Hemmerle et al. |
| 5,475,129 A | 12/1995 | Burke, Jr. et al. |
| 5,491,253 A | 2/1996 | Stuk et al. |
| 5,508,437 A | 4/1996 | Danho et al. |
| 5,525,733 A | 6/1996 | Novack et al. |
| 5,580,979 A | 12/1996 | Bachovchin |
| 5,587,372 A | 12/1996 | Aszodi et al. |
| 5,612,370 A | 3/1997 | Atwal |
| 5,616,776 A | 4/1997 | Stuk et al. |
| 5,627,283 A | 5/1997 | Stüber et al. |
| 5,646,036 A | 7/1997 | Schwall et al. |
| 5,679,842 A | 10/1997 | Kleiner |
| 5,686,292 A | 11/1997 | Schwall et al. |
| 5,688,992 A | 11/1997 | Burke, Jr. et al. |
| 5,698,731 A | 12/1997 | Bosetti et al. |
| 5,707,624 A | 1/1998 | Nickoloff et al. |
| 5,710,129 A | 1/1998 | Lynch et al. |
| 5,710,173 A | 1/1998 | Tang et al. |
| 5,712,395 A | 1/1998 | App et al. |
| 5,714,361 A | 2/1998 | Widlanski |
| 5,741,777 A | 4/1998 | Grinnell et al. |
| 5,753,687 A | 5/1998 | Mjalli et al. |
| 5,756,817 A | 5/1998 | Choi et al. |
| 5,773,411 A | 6/1998 | Wells et al. |
| 5,780,496 A | 7/1998 | Tang et al. |
| 5,786,454 A | 7/1998 | Waksman et al. |
| 5,789,427 A | 8/1998 | Chen et al. |
| 5,792,771 A | 8/1998 | App et al. |
| 5,792,783 A | 8/1998 | Tang et al. |
| 5,834,504 A | 11/1998 | Tang et al. |
| 5,843,997 A | 12/1998 | Heinz et al. |
| 5,849,693 A | 12/1998 | Wells et al. |
| 5,849,742 A | 12/1998 | App et al. |
| 5,880,141 A | 3/1999 | Tang et al. |
| 5,883,110 A | 3/1999 | Tang et al. |
| 5,883,113 A | 3/1999 | Tang et al. |
| 5,883,116 A | 3/1999 | Tang et al. |
| 5,886,020 A | 3/1999 | Tang et al. |
| 5,886,195 A | 3/1999 | Tang et al. |
| 5,891,917 A | 4/1999 | Tang et al. |
| 5,912,183 A | 6/1999 | Comoglio et al. |

(Continued)

FOREIGN PATENT DOCUMENTS

EP 0 339 549 A2 11/1989

(Continued)

OTHER PUBLICATIONS

"Brain Tumor" internet document accessed at <<http://www.intelihealth.com/IH/ihtIH/W/9339/31072.html>>; updated Jan. 25, 2008.*

(Continued)

*Primary Examiner*—Andrew D Kosar
(74) *Attorney, Agent, or Firm*—Leydig, Voit & Mayer, Ltd.

(57) ABSTRACT

Disclosed are compounds represented by the formula:

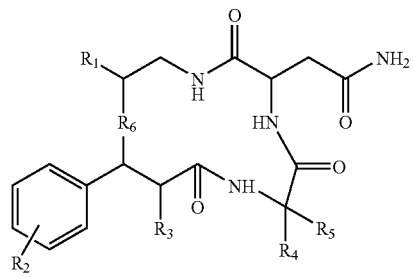

or a pharmaceutically acceptable salt or isomer thereof, wherein $R_1$-$R_6$ are as defined in the specification. These compounds are targeted for use as inhibitors of SH2 domain binding with a phosphoprotein, and are contemplated for use in a number of diseases including cancer. Also disclosed are pharmaceutical compositions comprising a compound of the invention and a pharmaceutically acceptable carrier.

21 Claims, 8 Drawing Sheets

U.S. PATENT DOCUMENTS

| | | | |
|---|---|---|---|
| 5,916,749 | A | 6/1999 | Bandman et al. |
| 5,922,697 | A | 7/1999 | Lunney et al. |
| 5,935,993 | A | 8/1999 | Tang et al. |
| 5,958,957 | A | 9/1999 | Andersen et al. |
| 5,965,558 | A | 10/1999 | Mjalli et al. |
| 5,972,978 | A | 10/1999 | Andersen et al. |
| 5,981,569 | A | 11/1999 | App et al. |
| 6,037,134 | A | 3/2000 | Margolis |
| 6,054,470 | A | 4/2000 | Betageri et al. |
| 6,136,542 | A | 10/2000 | Demers et al. |
| 6,228,986 | B1 | 5/2001 | Lanter et al. |
| 6,268,365 | B1 | 7/2001 | Betageri et al. |
| 6,284,768 | B1 | 9/2001 | Betageri et al. |
| 6,307,090 | B1 | 10/2001 | Burke, Jr. et al. |
| 6,355,614 | B1 | 3/2002 | Wallner |
| 6,559,137 | B1 | 5/2003 | Tung et al. |
| 2003/0118589 | A1 | 6/2003 | Sebti et al. |

FOREIGN PATENT DOCUMENTS

| | | |
|---|---|---|
| WO | WO 94/07913 | 4/1994 |
| WO | WO 95/11917 | 5/1995 |
| WO | WO 96/23813 | 8/1996 |
| WO | WO 97/08193 | 3/1997 |
| WO | WO 00/73326 | 12/2000 |
| WO | WO 01/70930 A2 | 9/2001 |
| WO | WO 02/16407 A2 | 2/2002 |
| WO | WO 2004/003005 A2 | 1/2004 |

OTHER PUBLICATIONS

S. Sriram and I. Steiner. Ann. Neurol. (2005) 58(6), pp. 939-945.*

Ye et al., "L-O-(2-Malonyl)tyrosine" A New Phosphotyrosyl Mimetic for the Preparation of Src Homology 2 Domain Inhibitory Peptides, J. Med. Chem. vol. 38, pp. 4270-4275, 1995.

Burke, Jr., et al., "4'-O-[2-(2-Fluoromalonyl)]-L-tyrosine: A Phosphotyrosyl Mimic for the Preparation of Signal Transduction Inhibitory Peptides", J. Med. Chem., vol. 39, pp. 1021-1027, Mar. 1, 1996.

Schoepfer et al., "Structure-based Design of Peptidomimetic Ligands of Grb2-SH2 Domain", Bioorganic & Medicinal Chemistry Letters 8, pp. 2865-2870, 1998.

Yao et al., "Potent Inhibition of Grb2 SH2 Domain Binding by Non-Phosphate-Containing Ligands", J. Med. Chem., vol. 42, pp. 25-35, 1999.

Gay et al., "Effect of Potent and Selective Inhibitors of the Grb2 SH2 Domain on Cell Motility", The Journal of Biological Chemistry, vol. 274, pp. 23311-23315, Aug. 13, 1999.

Schoepfer et al., "Highly Potent Inhibitors of the Grb2-SH2 Domain", Bioorganic & Medicinal Chemistry Letters 9, pp. 221-226, 1999.

Burke, Jr., et al., Monocarboxylic-Based Phosphotyrosyl Mimetics in the Design of Grb2 SH2 Domain Inhibitors, Bioorganic & Medicinal Chemistry Letters 9, pp. 347-352, 1999.

Gilmer et al., "Peptide Inhibitors of src SH3-SH2-Phosphorprotein Interactions", The Journal of Biological Chemistry, vol. 269, pp. 31711-31719, Dec. 16, 1994.

Charifson et al., "Peptide Ligands of pp60$^{c-src}$ SH2 Domains: A Thermodynamic and Structural Study", Biochemistry, vol. 36, pp. 6283-6293, 1997.

Liu et al., "Synthesis of L-2,3,5,6-Tetrafluoro-4-(Phosphonomethyl) Phenylalanine, a Novel Non-Hydrolyzable Phosphotyrosine Mimetic and L-4-(Phosphonodifluoromethyl)Phenylalanine", Tetrahedron Letters, vol. 38, pp. 1389-1392, 1997.

Cleland, "The Meerwein Reaction in Amino Acid Synthesis. II. An Investigation of Twenty-one Substituted Anilines", The Journal of Organic Chemistry, Vo., 34, pp. 744-747, Mar. 1969.

Gao et al., Inhibition of Grb2 SH2 Domain Binding by Non-Phosphate-Containing Ligands. 2. 4-(2-Malonyl)phenylalanine as a Potent Phosphotyrosyl Mimetic, J. Med. Chem., vol. 43, pp. 911-920, 2000.

Furet et al., Structure-Based Design and Synthesis of High Affinity Tripeptide Ligands of the Grb2-SH2 Domain, J. Med. Chem., vol. 41, pp. 3442-3449, 1998.

Tong et al., "Carboxymethyl-phenylalanine as a Replacement for Phosphotyrosine in SH2 Domain Binding", The Journal of Biological Chemistry, vol. 273, pp. 20238-20242 Aug. 7, 1998.

Kim et al., FEBS Lett, 453, 174-178, 1999.

Tulasne et al., "The Multisubstrate Docketing Site of the MET Receptor is Dispensable for MET-mediated RAS Signaling and Cell Scattering", Molecular Biology of the Cell. vol. 10, pp. 551-565, Mar. 1999.

Kim et al., "Dual Signaling Role of the Protein Tyrosine Phosphotase SHP-2 in Regulating Expression of Acute-Phase Plasma Proteins by Interleukin-6 Cytokine Receptors in Hepatic Cells", Molecular and Cellular Biology, vol. 19, pp. 5326-5338, Aug. 1999.

Nguyen et al., "Association of the Multisubstrate Docking Protein Gab1 with the Hepatocyte Growth Factor Receptor Requires a Functional Grb2 Binding Site Involving Tyrosine 1356", The Journal of Biological Chemistry, vol. 272, pp. 20811-20819, Aug. 15, 1997.

Maina et al., "Uncoupling of Grb2 from the Met Receptor in Vivo Reveals Complex roles in Muscle Development", Cell, vol. 87, pp. 531-542, Nov. 1, 1996.

Ponzetto et al., "Specific Uncoupling of GRB2 from the Met Receptor", The Journal of Biological Chemistry, vol. 271, pp. 14119-14123. Jun. 14, 1996.

Ettmayer et al., "Structural and Conformational Requirements for High-Affinity Binding to the SH2 Domain of Grb2", J. Med. Chem., vol. 42, pp. 971-980, 1999.

Royal et al., "Differential Requirement of Grb2 and P13-Kinase in HGF/SF-Induced Cell Motility and Tubulogenesis", Journal of Cellular Physiology, vol. 173, pp. 196-201, 1997.

Gao et al., Biorg & Med Chem Lett, 10, 923-927 (2000).

Burke, Jr., et al., "Preparation of . . . Peptide Synthesis", J. of Synthetic Organic Chem., No. 11, p. 1019, Nov. 11, 1991.

Burke, Jr., et al., "Potent Inhibition of Grb2 SH2 domain Binding by Non-Phosphate containing Ligands", First Annual Meeting on the Experimental Therapeutics of Human Cancer, Jun. 11-13, 1998, Hood College, Frederick Maryland (Summary).

Katunuma et al., "Use of new synthetic substrates for assays of cathepsin L and cathepsin B", J. Biochem. (Tokyo), vol. 93, pp. 1129-1135, 1983 (Abstract only).

Burke, Jr., et al., "Enantioselective Synthesis . . . Inhibitory Peptides", Tetrahedron, vol. 54, pp. 9981-9994, 1998.

Burke, Jr., et al., "Phosphotyrosyl-Based Motifs in the Structure-Based Design of Protein-Tyrosine Kinase-Dependent Signal Transduction Inhibitors", Current Pharmaceutical Design, vol. 3, pp. 291-304, 1997.

Burke, Jr., et al., "Nonhydrolyzable Phosphotyrosyl Mimetics for the Preparation of Phosphatase-Resistant SH2 Domain Inhibitors", Biochemistry, vol. 33, pp. 6490-6494, 1994.

Ye et al., "L-O-(2-Malonyl)tyrosine (L-OMT) a New Phosphotyrosyl Mimic Suitably Protected for Solid-Phase Synthesis of Signal Transduction Inhibitory Peptides", Tetrahedron Letters, vol. 36, pp. 4733-4736, 1995.

Kuriyan, "Modular Peptide recognition Domains in Eukaryotic Signaling", Annu. Rev. Biophys. Biomol. Struct., vol. 26, pp. 259-288, 1997.

Mayer et al., "Functions of SH2 and SH3 Domains", Protein modules in signal transduction, edited by A. J. Pawson, Berlin, New York, Springer, c1998, pp. 1-22.

Fry et al., "New insights into protein-tyrosine kinase receptor signaling complexes", Protein Science, vol. 2, pp. 1785-1797, 1993.

Levitzki, "Targeting signal transduction for disease therapy", Current Opinion in Cell Biology, vol. 8, pp. 239-244, 1996.

Boutin, "Tyrosine Protein Kinase Inhibition and Cancer", Int. J. Biochem., vol. 26, pp. 1203-1226, 1994.

Levitzki et al., "Tyrosine Kinase Inhibition: An Approach to Drug Development", Science, vol. 267, pp. 1782-1788, Mar. 24, 1995.

Lawrence et al., "Protein Kinase Inhibitors: The Tyrosine-specific Protein Kinases", Pharmacol. Ther., vol. 77, pp. 81-114, 1998.

Burke, Jr., et al., "Protein-Tyrosine Phosphatases: Structure, Mechanism, and Inhibitor Discovery", Biopolymers (Peptide Science), vol. 47, pp. 225-241 (1998).

Schoelson, "SH2 and PTB domain interactions in tyrosine kinase signal transduction", Current Opinion in Chemical Biology, vol. 1, pp. 227-234, 1997.

Waksman et al., "Crystal structure of the phosphotyrosine recognition domain Sh2 of v-src complexed with tyrosine-phosphorylated peptides", Nature, vol. 358, pp. 646-653, Aug. 20, 1992.

Waksman et al., "Binding of High Affinity Phosphotyrosyl Peptide to the Src SH2 Domain: Crystal Structures of the Complexed and Peptide-free Forms", Cell, vol. 72, pp. 779-790, Mar. 12, 1993.

Mikol et al., "The Crystal Structures of the SH2 Domain of p56$^{lck}$ Complexed with Two Phosphonopeptides Suggest a Gated Peptide Binding Site", J. Mol. Biol. vol. 246, pp. 344-355, 1995.

Hatada et al., "Molecular basis for interaction of the protein tyrosine kinase ZAP-70 with the T-cell receptor", Nature, vol. 377, pp. 32-38, Sep. 7, 1995.

Zhou et al., "Solution structure of the Shc SH2 domain complexed with a tyrosine-phosphorylated peptide from the T-cell receptor", Proc. Natl. Acad. Sci., vol. 92, pp. 7784-7788, Aug. 1995.

Narula et al., "Solution structure of the C-terminal SH2 domain of the human tyrosine kinase Syk complexed with a phosphotyrosine pentapeptide", Structure, vol. 3, 1061-1073, Oct. 15, 1995.

Xu et al., "Solution Structure of the Human pp60$^{c-src}$ SH2 Domain Complexed with a Phosphorylated Tyrosine Pentapeptide", Biochemistry, vol. 34, pp. 2107-2121, 1995.

Tong et al., "Crystal Structures of the Human p56$^{lck}$ SH2 Domain in Complex with Two Short Phosphotyrosyl Peptides at 1.0 Å and 1.8 Å Resolution", Academic Press Limited, 10 pages, 1996.

Sicheri et al., "Crystal structure of the Src family tyrosine kinase Hck", Nature, vol. 385, pp. 602-609, Feb. 13, 1997.

Chen et al., "Crystal Structure of a Tyrosine Phosphorylated STAT-1 Dimer Bound to DNA", Cell, vol. 93, pp. 827-839, May 29, 1998.

Songyang et al., "Recognition and specificity in protein tyrosine kinase-medicated signalling", Elsevier Science Ltd., pp. 470-475, 1995.

Lunney et al., "Structure-Based Design of a Novel Series of Nonpeptide Ligands That Bind to the pp60$^{src}$ SH2 Domain", J. Am. Chem. Soc., vol. 119, pp. 12471-12476, 1997.

Pacofsky et al., "Potent Dipeptide Inhibitors of the pp60$^{c-src}$ SH2 Domain", J. Med. Chem., vol. 41, pp. 1894-1908, 1998.

Marseigne et al., "Synthesis of New Amino Acids Mimicking Sulfated and Phosphorylated Tyrosine Residues", J. Org. Chem., vol. 53, pp. 3621-3624, 1988.

Domchek et al., "Inhibition of SH2 Domain/Phosphoprotein Association by a Nonhydrolyzable Phosphonopeptide", Biochemistry, vol. 31, pp. 9865-9870, 1992.

Xiao et al., "Syp (SH-PTP2) Is a Positive Mediator of Growth Factor-stimulated Mitogenic Signal Transduction", The Journal of Biological Chemistry, vol. 269, pp. 21244-21248, Aug. 19, 1994.

Wange et al., "F$_2$(Pmp)$_2$-TAMç$_3$, a Novel Competitive Inhibitor of the binding of ZAP-70 to the T Cell Antigen Receptor, Blocks Early T Cell Signaling", JBC Online, vol. 270, pp. 944-948, Jan. 13, 1995.

Rojas et al., "Controlling Epidermal Growth Factor (EGF)-stimulated Ras Activation in Intact Cells by a Cell-permeable Peptide Mimicking Phosphorylated EGF Receptor", The Journal of Biological Chemistry, vol. 271, pp. 27456-27461, Nov. 1, 1996.

Williams et al., "Selective Inhibition of Growth Faxtor-stimulated Mitogenesis by a Cell-permeable Grb2-binding Peptide", The Journal of Biological Chemistry, vol. 272, pp. 22349-22354, Aug. 29, 1997.

Stankovic, "The Role of 4-Phosphonodifluoromethyl- and 4-Phosphono-Phenylalanine in the Selectivity and Cellular Uptake of SH2 domain Ligands", Bioorganic & Medicinal Chemistry Letters, vol. 7, pp. 1909-1914, 1997.

Mehrotra et al., "α-Dicarbonyls as "Non-Charged" Arginine-Directed Affinity Labels", Bioorganic & Medicinal Chemistry Letters, vol. 6, pp. 1941-1946, 1996.

Margolis, "The GRB Family of SH2 domain Proteins", Prog. Biophys. Molec. Biol., vol. 62, pp. 223-244, 1994.

Burke, Jr., et al., "Preparation of Fluoro- and Hydroxy-4-(phosphonomethyl)-D,L-phenylalanine Suitably Protected for Solid-Phase Synthesis of Peptides Containing Hydrolytically Stable Analogues of O-Phosphotyrosine", Jour. Of Organic Chemistry, pp. 1336-1340, Mar. 12, 1993.

Burke, Jr., et al., "Synthesis of 4-Phosphono(difluoromethyl)-D,L-phenyllanine and N-Boc and N-Fmoc Derivatives Suitably Protected for solid-Phase Synthesis of Nonhydrolyzable Phosphotyrosyl Peptide Analogues", Tetrahedron Letters, vol. 34, pp. 4125-4128, 1993.

Smyth et al., "Enanthioselective Synthesis of N-Boc and N-Fmoc Protected Diethyl 4-Phosphono(difluoromethyl)-L-Phenylalanine; Agents Suitable for the Solid-Phase Synthesis of Peptides Containing Nonhydrolyzable Analogues of O-Phosphotyrosine", Tetrahedron letters, vol. 35, pp. 551-554, 1994.

Miller et al., "EPSP Synthase . . . 3-Phosphate Mimics", J. Organic & Medicinal Chem. Letters, vol. 3, No. 7, pp. 1435-1440, 1993.

"Synthesis and . . . containing peptides", Chem. Abs., vol. 123, No. 257331h, p. 1220, 1995.

Furet et al., "Discovery of 3-Aminobenzyloxycarbonyl as an N-Terminal Group conferring High Affinity to the Minimal Phosphopeptide Sequence Recognized by the Grb2-SH2 Domain", J. Med. Chem., vol. 40, pp. 3551-3556, 1997.

Rahuel et al., "Structural Basis for the High Affinity of Amino-Aromatic SH2 Phosphopeptide Ligands", J. Mol. Biol., 279, pp. 1013-1022, 1998.

Garcia-Echeverria et al., "Potent Antagonists of the SH2 Domain of Grb2: Optimization of the $X_{+1}$-Position of 3-Amino-Z-Tyr(PO$_3$H$_2$)-$X_{-1}$-Asn-NH$_2$", Journal of Medicinal Chemistry, vol. 41, pp. 1741-1744, May 21, 1998.

Rahuel et al., "Structural basis for specificity of GRB2-SH2 revealed by a novel ligand binding mode", Nature Structural Biology, vol. 3, No. 7, pp. 586-589, Jul. 7, 1996.

Oligino et al., "Nonphosphorylated . . . 2 Domain", The J. of Biological Chem., vol. 272, No. 46, pp. 29046-29052, Nov. 14, 1997.

Allen et al., "Tritiated Peptides. Part 15. Synthesis of Tritium Labelled Biologically Active Analogues of Somatostatin", J. Chem. Soc., Perkin Trans. 1, pp. 989-1003, 1986.

Ben-Levy et al., "A single autophosphorylation site confers oncogenicity to the Neu/ErbB-2 receptor and enables coupling to the MAP Kinase pathway", The EMBO Journal, vol. 13, pp. 3302-3311, 1994.

Dankort et al., Distinct Tyrosine Autophosphorylation Sites Negatively and Positively Modulate New-Mediated Transformation, Molecular and Cellular Biology, vol. 17, pp. 5410-5425, Sep. 1997.

Ma et al., "Bcr phosphorylated on tyrosine 177 binds Grb2", Oncogene, vol. 14, pp. 2367-2372, 1997.

DiFiore et al., "Overexpression of the Human EGF Receptor confers an EGF-Dependent Transformed Phenotype to NIH 3T3 Cells", Cell, vol. 51, pp. 1063-1070, Dec. 24, 1987.

Hudziak et al, "Increased expression of the putative growth factor receptor p185$^{HER2}$ causes transformation and tumorigenesis of NIH 3T3 cells", Proc. Natl. Acad. Sci., vol. 84, pp. 7159-7163, Oct. 1987.

Kraus et al., "Overexpression of the EGF receptor-related proto-oncogene erbB-2 in human mammary tumor cells lines by different molecular mechanisms", The EMBO Journal, vol. 6, pp. 605-610, 1987.

Sastry et al., "Quantitative analysis of Grb2-Sos1 interaction: the N-terminal SH3 domain of Grb2 mediates affinity", Oncogene, 11, pp. 1107-1112, 1995.

Searles, The Reaction of Trimethylene Oxide with Grignard Reagents and Organolithium Compounds, J. Amer. Chem. Soc., vol. 73, pp. 124-125, 1951.

Fretz et al., "Targeting a Hydrophobic Patch on the Surface of the Grb2-SH2 Domain", 15$^{th}$ Amer. Peptide Symposium, Nashville, TN, Jun. 1997, Abstract No. P422.

Fixman et al., "Efficient Cellular . . . Proteins, Cb1 and Gab1", The J. of Biological Chem., vol. 272, No. 32, pp. 20167-20172, Aug. 8, 1997.

Tari et al., "Inhibition of Grb2 . . . Leukemic Cells", Biochemical and Biophysical Research Communications, vol. 235, pp. 383-388, Article No. RC976791, 1997.

Xie et al., "Dominant-negative Mutants . . . Rat HER-2/Neu", The J. of Biological Chem., vol. 270, No. 51, pp. 30717-30724, Dec. 22, 1995.

Maignan et al., "Crystal Structure of the Mammalian Grb2 Adaptor", Science, vol. 268, pp. 291-293, Apr. 14, 1995.

Saltiel et al., "Targeting signal transduction in the discovery of antiproliferative drugs", Chemistry & Biology, vol. 3, No. 11, pp. 887-893, Nov. 1996.

McNemar et al., Thermodynamic and . . . Binding to Grb2-SH2:, Biochemistry, vol. 36, pp. 10006-10014, 1997.

Ogura et al., "Conformation of an . . . Grb2 SH2 domain", J. of Biomolecular NMR, vol. 10, pp. 273-278, 1997.

Gay et al., "Dual Specificity of . . . Peptide Ligands", Biochemistry, vol. 36, pp. 5712-5718, 1997.

Bobko et al., "CD45 Protein . . . Irreversible Inhibitors", Bioorganic & Medicinal Chem. Letters, vol. 5, No. 4, pp. 353-356, 1995.

Burke et al., "Conformationally Constrained . . . 2 Domain Inhibitors", J. Med. Chem., vol. 38, pp. 1386-1396, 1995.

Chemical Abstracts, vol. 122, p. 424, 1995 (Abs. No. 258899).

Gordeev et al., "N-α-Fmoc-4-Phosphono(difluoromethyl)-L-phenylalanine: . . . into Peptides", Tetrahedron Letters, vol. 35, pp. 7585-7588, 1994.

Kitas et al., "Synthesis of O-Phosphotyrosine . . . Deportection Procedures", J. Org. Chem., vol. 55, pp. 4181-4187, 1990.

Chemical Abstracts, vol. 124, No. 1, p. 1004, 1996 (Abs. No. 9413).

Morelock et al., "Determination of Receptor . . . Phosphotyrosyl Peptides", J. of Med. Chem., vol. 38, pp. 1309-1318, 1995.

Shahripour et al., "Novel Phosphotyrosine . . . Domain", Bioorganic & Medicinal Chem. Letters, vol. 6, No. 11, pp. 1209-1214, 1996.

Rojas et al., "An Alternative . . . SH2 Domain", Biochemical and Biophysical Research Communications, vol. 234, pp. 675-680, 1997.

Gao et al., "Macrocyclization in the design of a conformationally constrained Grb2 SHG2 domain inhibitor", Bioorganic & Medicinal Chemistry Letters, 11:1889-1892 (2001).

Gao et al., "Olefin Metathesis in the Design and Synthesis of a Globally constrained Grb2 SH2 Domain Inhibitor", Organic Letters, 3:1617-1620 (2001).

* cited by examiner

SH2 DOMAIN BINDING INHIBITORS

CROSS-REFERENCE TO A RELATED PATENT APPLICATION

This patent application is a continuation of co-pending U.S. patent application Ser. No. 10/944,699, filed Sep. 17, 2004, which claims the benefit of U.S. Provisional Patent Application No. 60/504,241, filed Sep. 18, 2003. The disclosure of the '699 application is incorporated by reference.

FIELD OF THE INVENTION

This invention relates to macrocyclic peptides, a composition comprising such macrocyclic peptides, and a method of using the peptides, e.g., in inhibiting SH2 domain binding with a phosphoprotein such as in the prevention or treatment of a disease, state, or condition in a mammal.

BACKGROUND OF THE INVENTION

The pharmaceutical industry is in search for new classes of compounds for the therapy and prophylaxis of proliferative diseases such as cancer, autoimmune diseases, and hyperproliferative skin disorders such as psoriasis. These diseases or disorders affect a large portion of the population, leading to suffering and possibly death.

Some of these diseases or disorders may involve signal transduction. Signal transduction is found in normal cellular homeostasis and is the process of relaying extracellular messages, e.g., chemical messages in the form of growth factors, hormones and neurotransmitters, via receptors, e.g., cell-surface receptors, to the interior of the cell. Protein-tyrosine kinases play a central role in this biological function. Among others, these enzymes catalyze the phosphorylation of specific tyrosine residues to form tyrosine phosphorylated residues. Examples of this class of enzymes include the PDGF receptor, the FGF receptor, the HGF receptor, members of the EGF receptor family such as the EGF receptor, erb-B2, erb-B3 and erb-B4, the src kinase family, Fak kinase and the Jak kinase family. The tyrosine-phosphorylated proteins are involved in a range of metabolic processes, from proliferation and growth to differentiation.

Protein-tyrosine phosphorylation is known to be involved in modulating the activity of some target enzymes as well as in generating specific complex networks involved in signal transduction via various proteins containing a specific amino acid sequence called a Src homology region or SH2 domain (see Proc. Natl. Acad. Sci. USA, 90, 5891 (1990)). A malfunction in this protein-tyrosine phosphorylation through tyrosine kinase overexpression or deregulation is manifested by various oncogenic and (hyper-) proliferative disorders such as cancer, inflammation, autoimmune disease, hyper-proliferative skin disorders, such as psoriasis, and allergy/asthma.

SH2- and/or SH3-comprising proteins that play a role in cellular signaling and transformation include, but are not limited to, the following: Src, Lck, Eps, ras GTPase-activating protein (GAP), phospholipase C, phosphoinositol-3 (P1-3)kinase, Fyn, Lyk, Fgr, Fes, ZAP-70, Sem-5, p85, SHPTP1, SHPTP2, corkscrew, Syk, Lyn, Yes, Hck, Dsrc, Tec, Atk/Bpk, Itk/Tsk, Arg, Csk, tensin, Vav, Emt, Grb2, BCR-Abl, Shc, Nck, Crk, CriL, Syp, Blk, 113TF, 91TF, Tyk2, especially Src, phospholipase c, phosphoinositol-3 (p1-3)kinase, Grb2, BCR-Abl, Shc, Nck, Crk, CriL, Syp, Blk, 113TF, 91TF, and Tyk2. A direct link has been established between activated receptor kinases and Ras with the finding that the mammalian Grb2 protein, a 26 kilodalton (kD) protein comprising a single SH2 and two SH3 domains bind to proline-rich sequences present in the Sos exchange factor.

The significance of ras-regulatory proteins in human tumors is also highlighted by the role of Grb2 in BCR-Abl mediated oncogenesis (J. Exp. Med., 179, 167-175 (1994)). Relating to the binding of SH2 domains with phosphotyrosine ("pTyr") containing ligands is the interaction of the doubly ionized pTyr phosphate with two invariant arginine residues in a well-formed pocket. These arginine-phosphate interactions are related to the overall binding, such that high affinity binding is usually lost by removal of the phosphate group. International Publication Nos. WO 02/16407, WO 2004/003005, WO 00/73326 and WO 00/56760 disclose certain SH2 domain binding inhibitors, the disclosures of which are incorporated herein in their entireties by reference.

There exists a need for molecules that have an ability to mimic the structure of the phosphotyrosine peptide binding site, as well as a need for compounds that have the ability to disrupt the interaction between SH2 domains of proteins (e.g., regulatory proteins) for example that of Grb2, and proteins with phosphorylated moieties. There further exists a need for compounds suitable for use in the therapy or prophylaxis of proliferative diseases or conditions, as well as in diagnosis, assays, and testing.

These and other advantages of the present invention will be apparent from the description as set forth below.

BRIEF SUMMARY OF THE INVENTION

The present invention provides SH2 domain binding inhibiting compounds or a pharmaceutically acceptable salt or stereoisomer(s) thereof. The compounds of the present invention have an advantage that their conformation is constrained to provide attractive binding affinity with a SH2 domain protein.

The present invention further provides a pharmaceutical composition comprising a pharmaceutically or pharmacologically acceptable carrier and a compound of the present invention. The present invention also provides a method for inhibiting an SH2 domain from binding with a phosphoprotein comprising contacting an SH2 domain with a compound of the present invention. The present invention also provides a method of preventing or treating a disease, state, or condition, which is mediated by the binding of an SH2 domain-containing protein with a phosphoprotein, by the use of the compounds of the invention.

DETAILED DESCRIPTION OF THE INVENTION

Figure 1A:
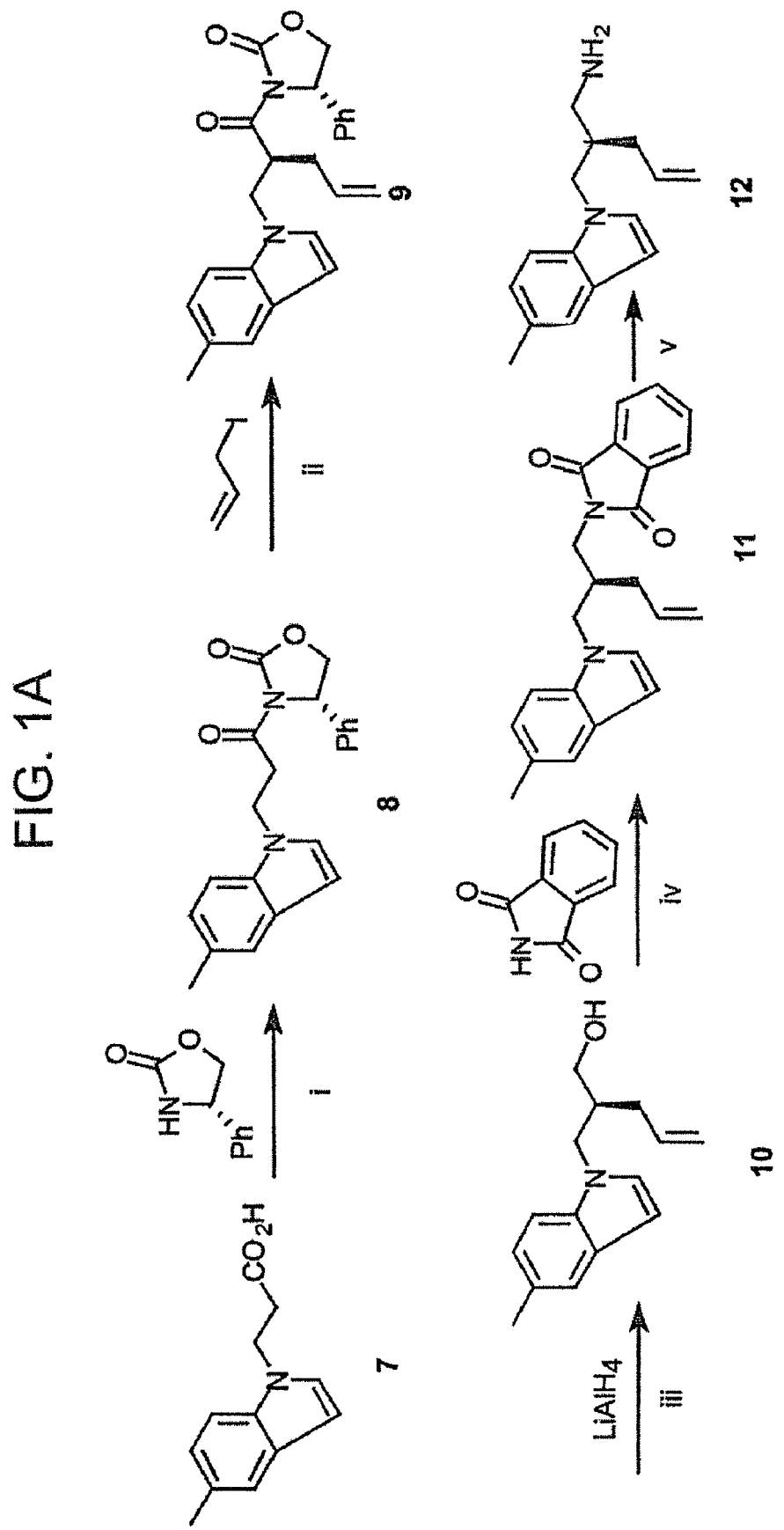
FIG. 1A depicts a method of preparing compounds 8-12 which may find use as intermediates for preparing compounds 5-6 of the present invention. Reagents and conditions: (i) $Me_3CCOCl$, N-methyl morpholine, BuLi, THF, $-78°$ C., 2 h, (87% yield); (ii) LHMDS, THF, $-78°$ C., 2 h, (69% de in 61% yield); (iii) $LiAlH_4$, THF, $-78°$ C., 1 h then $0°$ C. 3 h, (92% yield); (iv) DIAD, $Ph_3P$, THF, rt, 12 h, (88% yield); (v) $N_2H_4·H_2O$, EtOH, $H_2O$, reflux, 3 h, (84% yield).

An aspect of the present invention is predicated on the concept that binding affinity for SH2 domain proteins can be envisioned to increase by a conformational constraint in a ligand. The conformational constraint is believed to lead to certain advantages, e.g., a reduction in binding entropy penalty. Binding of natural pTyr-containing ligands to Grb2 SH2 domains takes place in a β-bend fashion, with key interactions occurring in a pTyr binding pocket as well as in a proximal pocket which ligates the amino acid side chain of a pY+2 Asn residue. The present invention provides a novel platform which is expected provide enhanced binding outside the pTyr pocket.

Accordingly, the present invention provides a compound of the formula I:

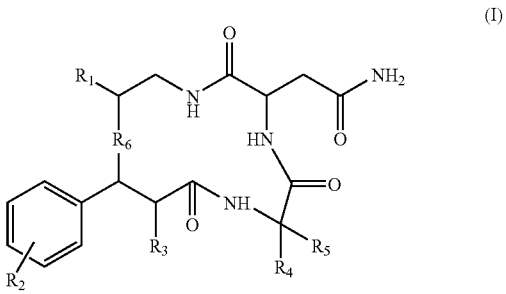

wherein $R_1$ is $C_6$-$C_{14}$ aryl heterocyclyl $C_1$-$C_6$ alkyl, whose aryl moiety is substituted with one or more groups selected from the group consisting of $C_1$-$C_6$ alkyl, halo, hydroxy, amino, $C_1$-$C_6$ alkoxy, and hydroxy $C_1$-$C_6$ alkyl;

$R_2$ is carboxy $C_1$-$C_6$ alkyl, carboxy $C_1$-$C_6$ alkylamino, oxalylamino, carboxy $C_1$-$C_6$ alkoxy, dicarboxy $C_1$-$C_6$ allyl, dicarboxy $C_1$-$C_6$ alkyloxy, dicarboxyhalo $C_1$-$C_6$ alkyl, dicarboxyhalo $C_1$-$C_6$ alkyloxy, RSO₂NH— wherein R is $C_1$-$C_6$ alkyl, halo $C_1$-$C_6$ alkyl, $C_6$-$C_{14}$ aryl, $C_6$-$C_{14}$ aryl $C_1$-$C_6$ alkyl, or trifluoro $C_1$-$C_6$ alkyl, phosphono, phosphono $C_1$-$C_6$ allyl, phosphonohalo $C_1$-$C_6$ alkyl, $C_6$-$C_{14}$ aryl $C_1$-$C_6$ alkyl phosphino $C_1$-$C_6$ alkyl, $C_1$-$C_6$ alkyl phosphino $C_1$-$C_6$ alkyl, phosphoryl, phosphoryl $C_1$-$C_6$ alkyl, phosphoryl $C_1$-$C_6$ alkoxy, $C_6$-$C_{14}$ aryl, or $C_6$-$C_{14}$ aryl $C_1$-$C_6$ alkyl, wherein the aryl and alkyl moieties may be optionally substituted with a substituent selected from the group consisting of halo, hydroxy, carboxyl, amino, amino $C_1$-$C_6$ alkyl, $C_1$-$C_6$ alkyl, $C_1$-$C_6$ alkoxy, and keto;

$R_3$ is hydrogen, azido, amino, carboxy $C_1$-$C_6$ alkyl, $C_1$-$C_6$ alkoxycarbonyl $C_1$-$C_6$ alkyl, aminocarbonyl $C_1$-$C_6$ alkyl, or $C_1$-$C_6$ alkylcarbonylamino, wherein the alkyl portion of $R_3$ may be optionally substituted with a substituent selected from the group consisting of halo, hydroxy, carboxyl, amino, amino $C_1$-$C_6$ alkyl, $C_1$-$C_6$ alkyl, $C_1$-$C_6$ alkoxy, and keto;

$R_4$ and $R_5$, are independently selected from the group consisting of hydrogen, $C_1$-$C_6$ alkyl, $C_3$-$C_8$ cycloalkyl, and heterocyclyl, or $R_4$ and $R_5$ together form a $C_3$-$C_8$ cycloalkyl or heterocyclyl; and $R_6$ is a linker;

said heterocyclyl is a 4-7 membered ring comprising at least one hetero atom selected from the group consisting of O, N, and S;

or a pharmaceutically acceptable salt, stereoisomer, or mixture of stereoisomers thereof.

Examples of "aryl" include phenyl, naphthyl, anthracenyl, fluorenyl, biphenyl, dihydronaphthyl, tetrahydronaphthyl, and the like. Examples of "heterocyclyl" include pyrrolyl, furanyl, pyrenyl, thienyl, pyridyl, pyrazinyl, pyrazolyl, imidazolyl, pyradazinyl, pyrimidinyl, triazinyl, pyranyl, thiazolyl, isothiazolyl, pteridinyl, piperonyl, triazolyl, tetrazolyl, oxazolyl, oxadiazolyl, thiadiazolyl, and the like. The aryl and heterocyclyl moieties may be fused, such as, e.g., indole, isoindole, benzimidazole, quinoline, isoquinolinyl, benzoxazolyl, benzofuranyl, isobenzofuranyl, carbazolyl, benzodioxolyl, and the like. The term "halo" refers to fluoro, chloro, bromo, or iodo. When an aryl group is substituted, the substituent can be located at any of the available positions; for example, in indolyl, the phenyl ring can be substituted at 3, 4, 5, or 6-positions, particularly the 5-position.

In accordance with an embodiment of the invention, $R_1$ is $C_6$-$C_{14}$ aryl heterocyclyl $C_1$-$C_6$ alkyl, whose aryl moiety is substituted with $C_1$-$C_6$ alkyl. Thus, for example, $R_1$ is a phenyl heterocyclyl $C_1$-$C_6$ alkyl whose aryl moiety is substituted with $C_1$-$C_6$ alkyl. In a specific example, $R_1$ is a phenyl heterocyclyl methyl whose aryl(phenyl) moiety is substituted with $C_1$-$C_6$ alkyl, particularly a methyl group; thus, $R_1$ can be methyl indolyl methyl.

In the compounds of the above embodiments, $R_2$ is selected from the group consisting of carboxy $C_1$-$C_6$ alkyl, oxalylamino, dicarboxy $C_1$-$C_6$ alkyl, $RSO_2NH$— wherein R is $C_1$-$C_6$ alkyl, halo $C_1$-$C_6$ alkyl, $C_6$-$C_{14}$ aryl, $C_6$-$C_{14}$ aryl $C_1$-$C_6$ alkyl, or trifluoro $C_1$-$C_6$ alkyl, phosphono $C_1$-$C_6$ alkyl, phosphonohalo $C_1$-$C_6$ alkyl, $C_6$-$C_{14}$ aryl $C_1$-$C_6$ alkyl phosphino $C_1$-$C_6$ alkyl, $C_1$-$C_6$ alkyl phosphino $C_1$-$C_6$ alkyl, $C_6$-$C_{14}$ aryl, and $C_6$-$C_4$ aryl $C_1$-$C_6$ alkyl, wherein the aryl and alkyl moieties may be optionally substituted with a substituent selected from the group consisting of halo, hydroxy, carboxyl, amino, amino $C_1$-$C_6$ alkyl, $C_1$-$C_6$ alkyl, $C_1$-$C_6$ alkoxy, and keto.

Specifically, $R_2$ is selected from the group consisting of carboxy $C_1$-$C_6$ alkyl, oxalylamino, dicarboxy $C_1$-$C_6$ alkyl, $RSO_2NH$— wherein R is $C_1$-$C_6$ alkyl, halo $C_1$-$C_6$ alkyl, $C_6$-$C_{14}$ aryl, $C_6$-$C_{14}$ aryl $C_1$-$C_6$ alkyl, or trifluoro $C_1$-$C_6$ alkyl, phosphono $C_1$-$C_6$ alkyl, phosphonohalo $C_1$-$C_6$ alkyl, $C_6$-$C_{14}$ aryl $C_1$-$C_6$ alkyl phosphino $C_1$-$C_6$ alkyl, and $C_1$-$C_6$ alkyl phosphino $C_1$-$C_6$ alkyl. Particular examples of $R_2$ can be carboxy methyl, oxalylamino, dicarboxy methyl, phosphono methyl, benzyl phosphino methyl, and methyl phosphinomethyl.

In any of the embodiments described above, $R_3$ can be selected from the group consisting of carboxy $C_1$-$C_6$ alkyl, wherein the alkyl portion may be optionally substituted with a substituent selected from the group consisting of halo, hydroxy, carboxyl, amino, amino $C_1$-$C_6$ alkyl, $C_1$-$C_6$ alkyl, $C_1$-$C_6$ alkoxy, and keto; particularly, $R_3$ is carboxy $C_1$-$C_6$ alkyl, wherein the alkyl portion may be optionally substituted with hydroxy, such as for example, compounds wherein $R_3$ is carboxy methyl or carboxy hydroxymethyl.

In any of the embodiments described above, $R_4$ and $R_5$ together form a $C_3$-$C_8$ cycloalkyl, for example, cyclohexyl.

In any of the embodiments described above, $R_6$ is a $C_2$-$C_4$ alkylenyl, $C_2$-$C_4$ alkenylenyl, or $C_2$-$C_4$ alkenylenyl, which may optionally substituted, particularly, $R_6$ is a $C_2$-$C_4$ alkenylenyl, e.g., $C_3$ alkenylenyl.

Specific examples of the compounds of the present invention are:

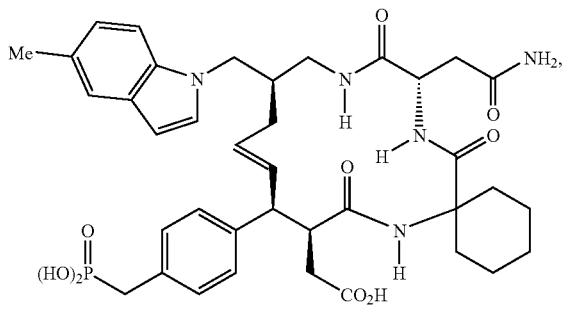

(5)

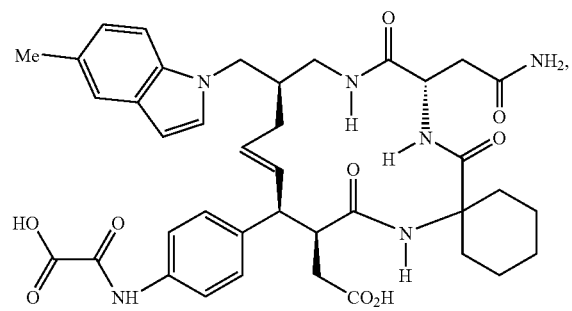

(28)

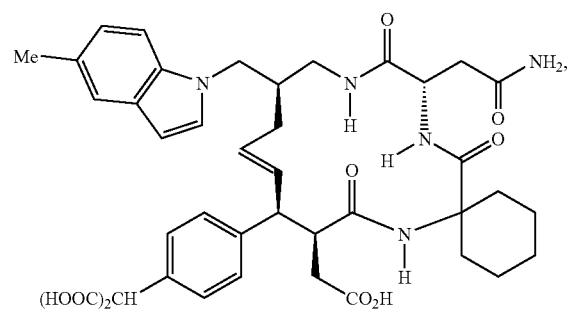

(32)

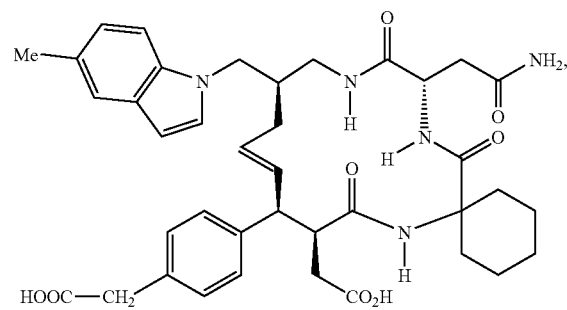

(33)

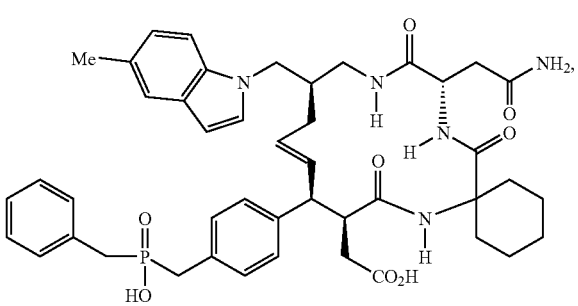

(41)

-continued

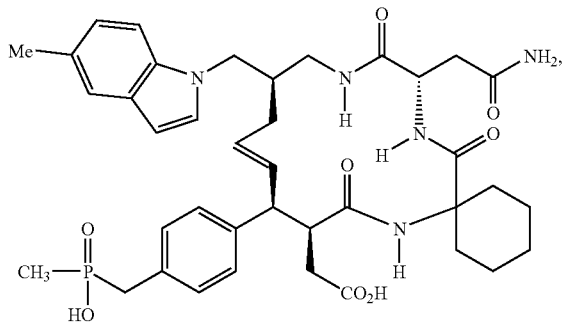

(49)

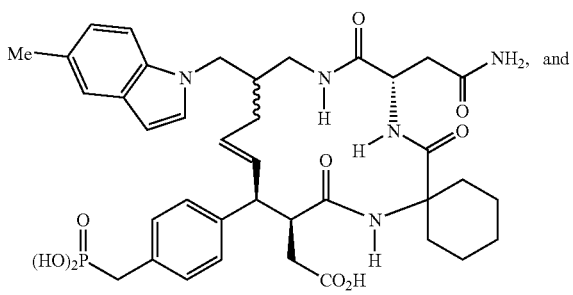

(61)

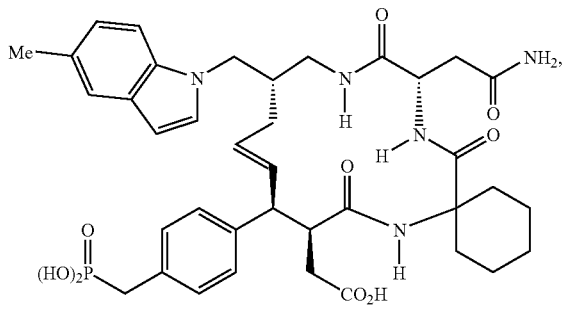

(62)

or a pharmaceutically acceptable salt or stereoisomer thereof.

Figure 1B:
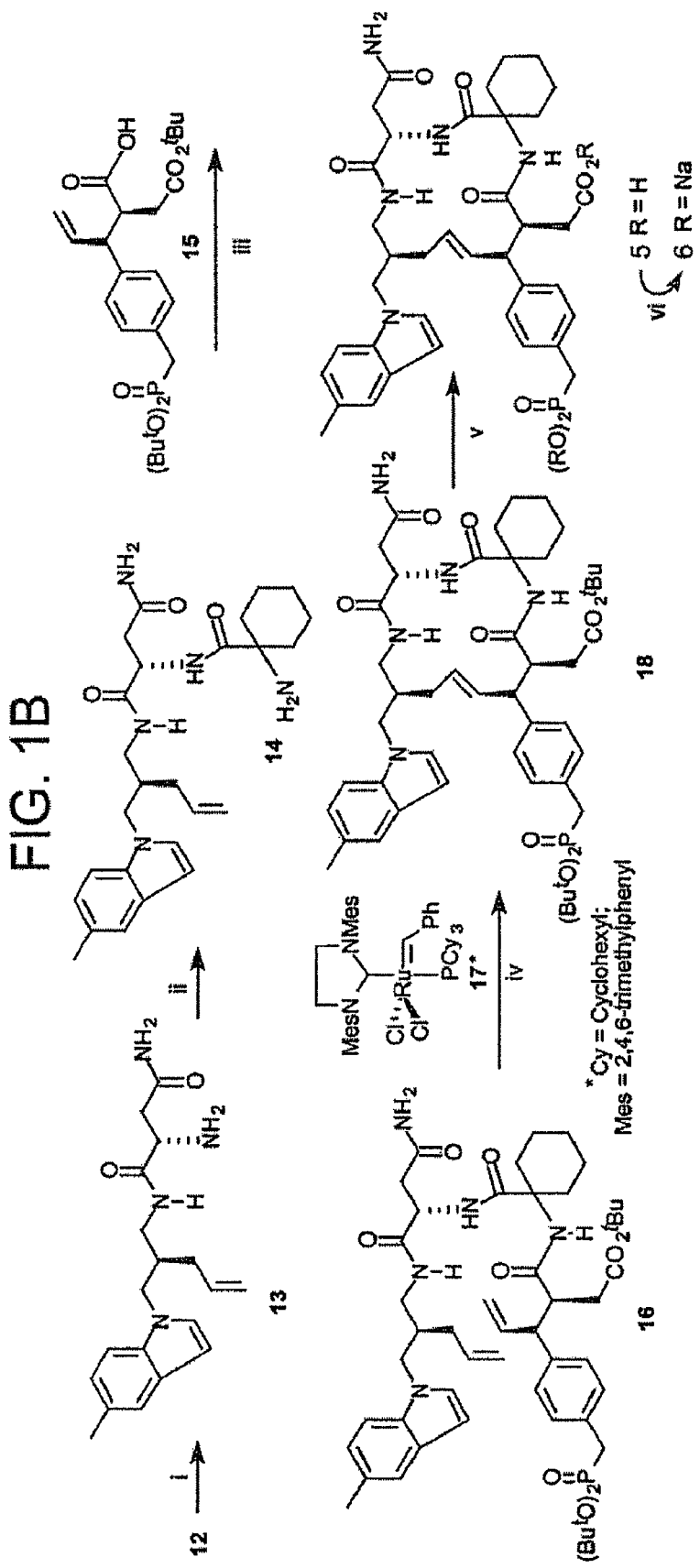
FIG. 1B depicts a method of preparing compounds 5-6 of the present invention. Reagents and conditions: (i) (a) Boc-Asn-OH, DIPCDI, HOBt, rt, 12 h; (b) $HCl_{(aq)}$ (2N), $CH_3CN$, rt, 12 h, (75% yield); (ii) (a) N-Fmoc $Ac_6c$, EDCI.HCl, HOBt, rt, 12 h (83% yield); (b) piperidine, $CH_3CN$, rt, 2 h, (86% yield); (iii) 15,[16] EDCI.HCl, HOAt, DMF, $50°$ C., 24 h (56% yield); (iv) 17, $CH_2Cl_2$, reflux, 48 h (70% yield); (v) TFA-HS$(CH_2)_2$SH—$H_2O$, rt, 1 h (35% yield); (vi) aq. $NaHCO_{3(aq)}$ (quantitative).
Figure 2:
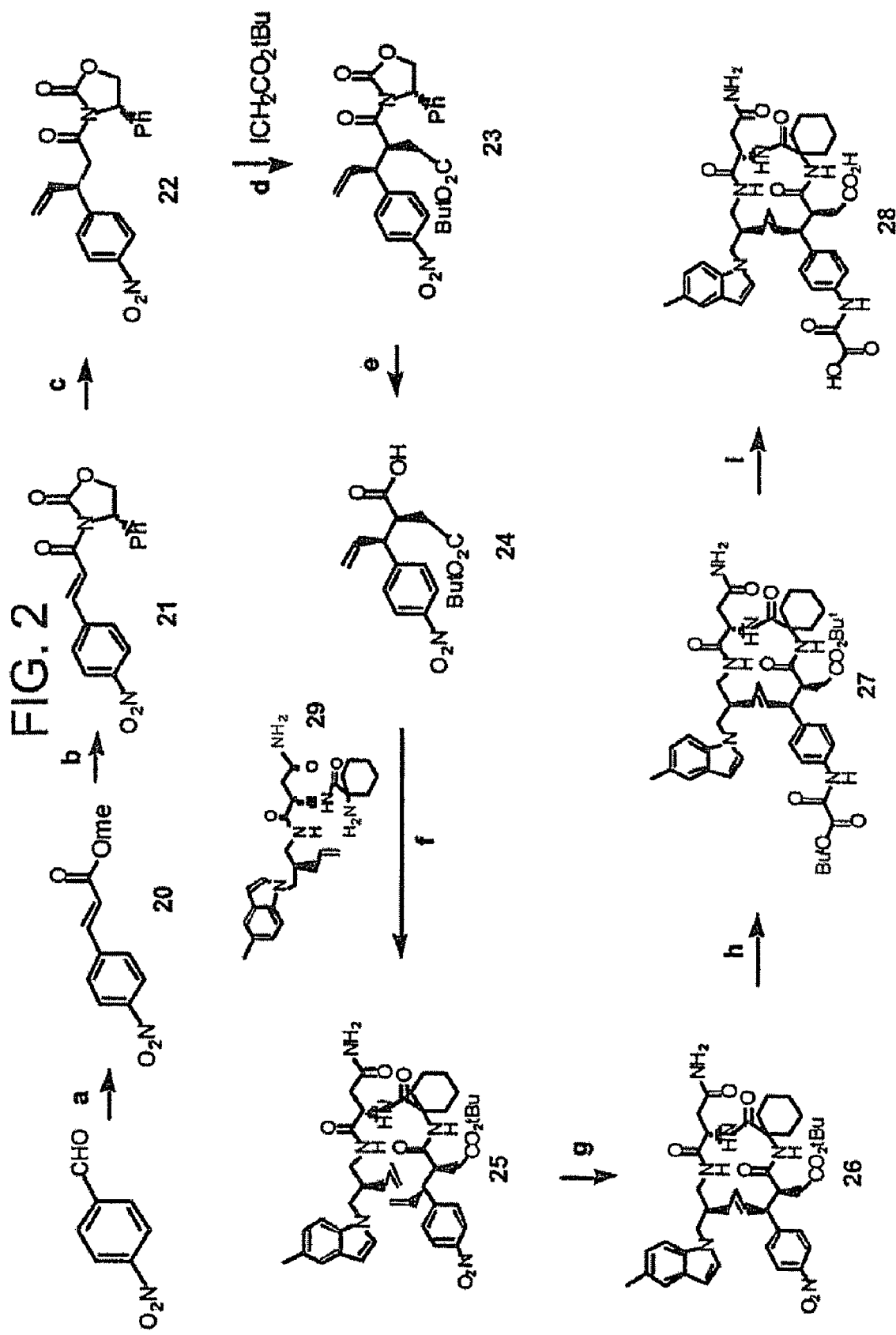
FIG. 2 depicts a method of preparing compound 28 of the present invention. Reagents and conditions: (a) Trimethylphophoacetate, NaH, eter, 0° C.-rt, overnight, 86% (b) (i) LiOHH₂O, THF/H₂O/MeOH, rt 2.5 hr., 92% (ii) Trimethylacetylchloride, N-methyl morpholine, S-(+)-Phenyl-2-oxazolidone, n-BuLi, THF, 81% (c) Vinylmagnesium bromide, PhSCu, Ether, THF, 23% (d) LHMDS, THF, −78° C.-rt, 2 hr., 56% (e) LiOHH₂O. H₂O₂, THF/H₂O, rt 6 hr., 95% (f) EDCI HCl, HOBt, DIPEA, THF, rt 36 hr., 52% (g) 2$^{nd}$ Grubbs, CH₂Cl₂, 65-68° C. for 24 hr., quant. (h) (i) Al—Hg, ether, H₂O, reflux at 65-70° C. for 1.5 hr. (ii) I13 PR═₂Net, CH₂Cl₂, 0° C.-rt for 3 hr., 48% for 2 steps (i) TFA, H₂O, EDT, rt, 1.2 hr., 16%.
Figure 3:
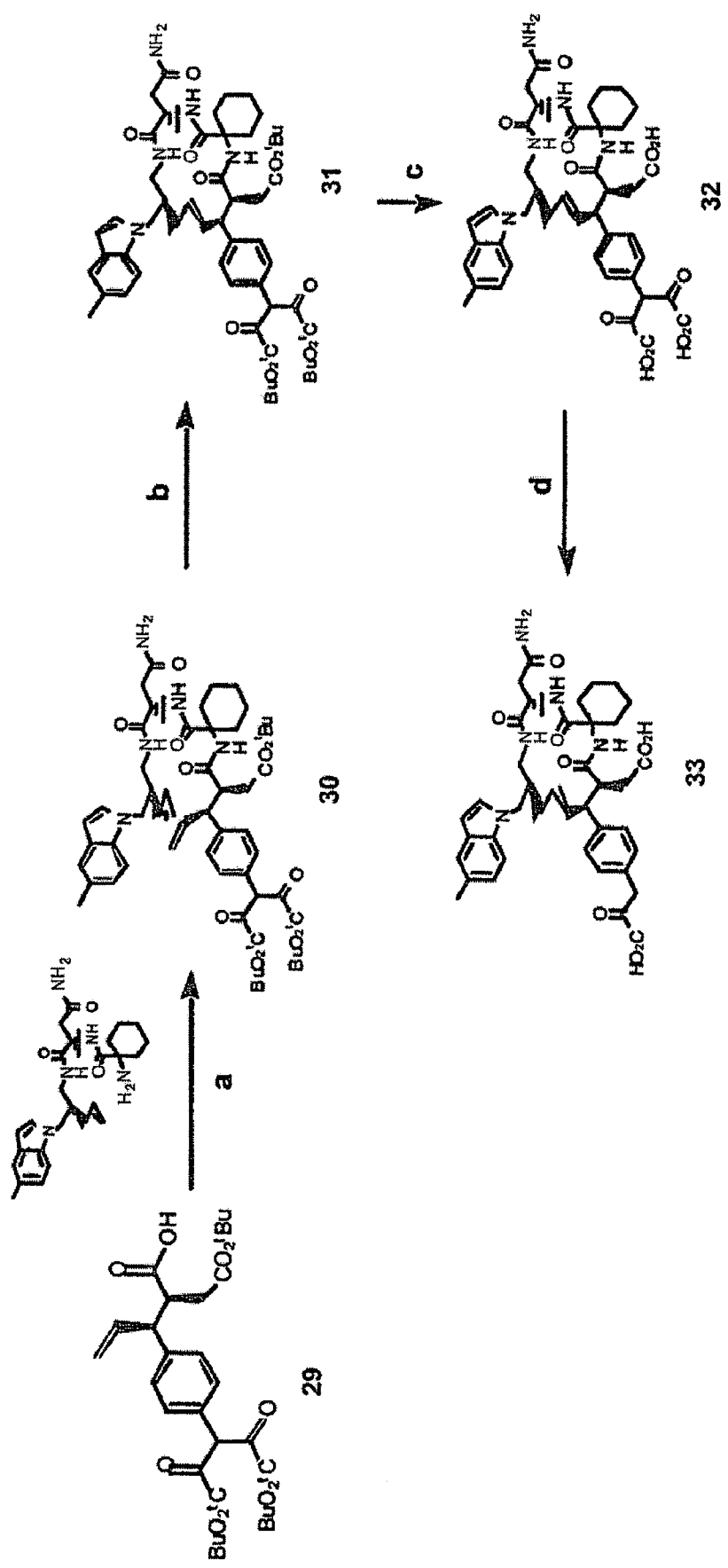
FIG. 3 depicts a method of preparing compounds 32-33 of the present invention. Reagents and conditions: (a) EDCI HCl, HOAt, DMF, 70-75° C., 22 hr., 19% (b) 2$^{nd}$ Grubbs, CH₂Cl₂, 66-67° C. for 23 hr., 81% (c) TFA, H₂O, EDT, rt, 1.5 hr., 38% (d) LiOH H₂O, rt, 4 hr., 19%.
Figure 4:
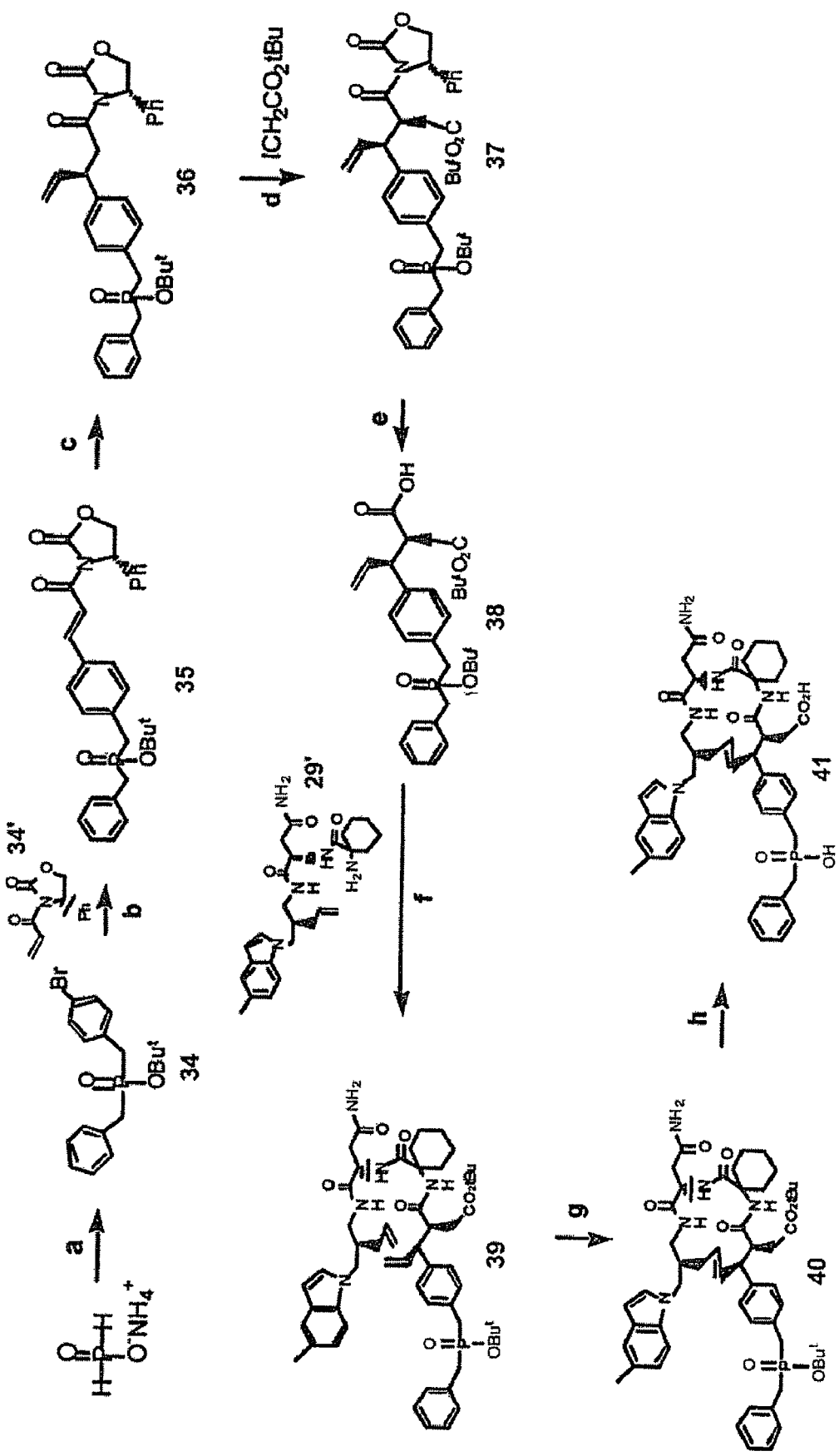
FIG. 4 depicts a method of preparing compound 41 of the present invention. Reagents and conditions: (a) (i) Benzylbromide, hexamethyldisilazane, 4-bromobenzylbromide, CH₂Cl₂ (ii) t-Butyl, 2,2,2-trichloracetimidate, CH₂Cl₂, BF₃.Oet₂ (b) PD(OAc)₂, tri-o-tolyphosphine, Et₃N, 120° C., 1.5 hr. 92% (c) Vinylmagnesium bromide, PhSCu, Ether, THF, 44% (d) NaHMDS, THF, −78° C.-rt, 2 hr., 40% (d) LiOH.H₂O.H₂O₂, THF/H₂O, rt 4 hr., 85% (f) EDCl-HCL, HOAt, DMF, 40-45° C., 30 hr., 42% (g) 2$^{nd}$ Grubbs, CH₂Cl₂, 65-68° C. for 20 hr., 88% (h) TFA, H₂O, EDT, rt, 1.2 hr., 36%.
Figure 5:
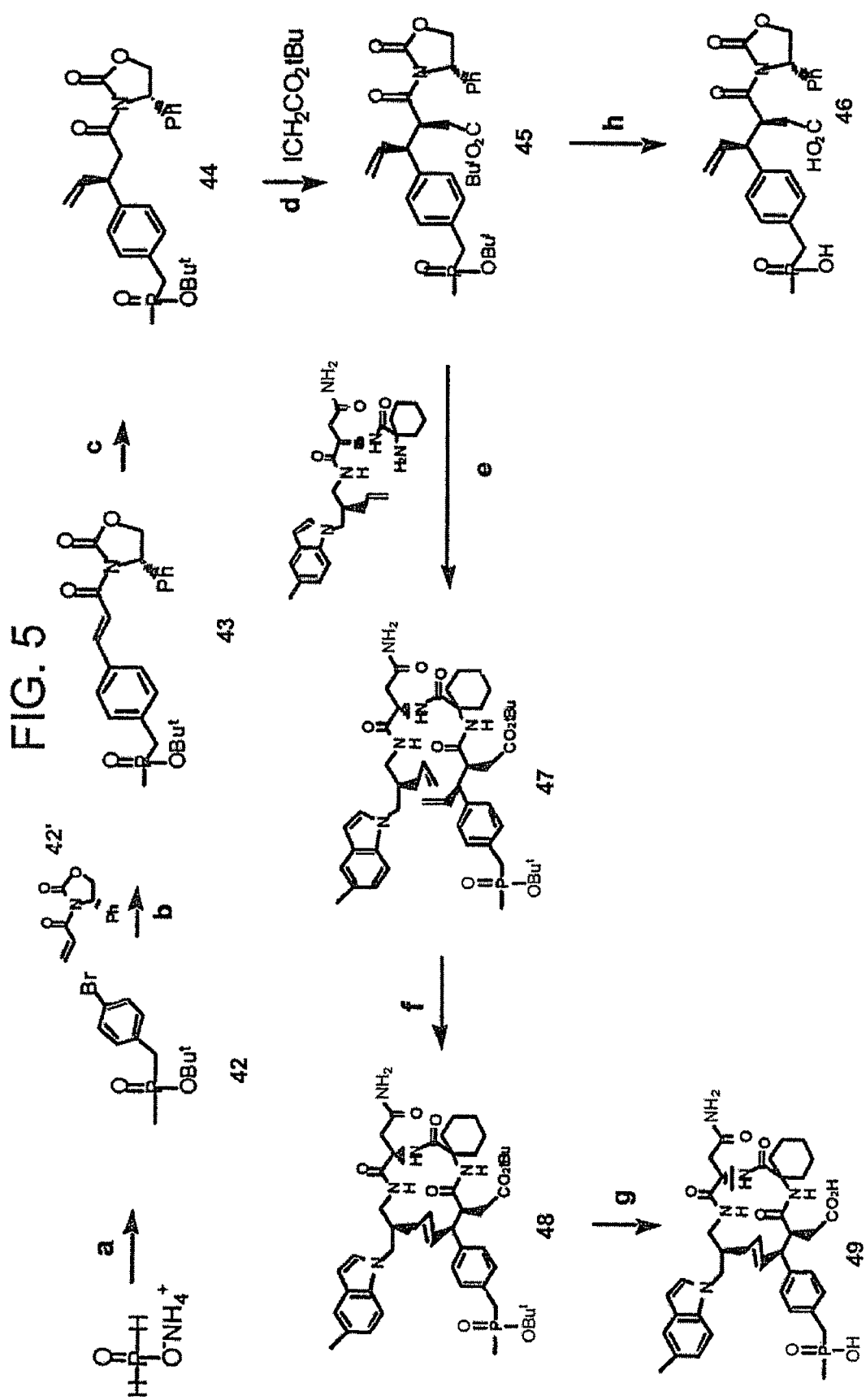
FIG. 5 depicts a method of preparing compound 49a of the present invention. Reagents and conditions: (a) (i) hexamethyldisilazane, 4-bromobenzylbromide, iodomethane, CH₂Cl₂, (ii) t-Butyl, 2,2,2-trichloracetimidate, CH₂Cl₂, BF₃.Oet₂, 33% for two steps (b) PD(OAc)₂, tri-o-tolyphosphine, Et₃N, 115° C., 1.5 hr. 73% (c) Vinylmagnesium bromide, PhSCu, Ether, THF/CH₂Cl₂, 76% (d) NaHMDS, THF, −78° C.-rt, 0.5 hr., 61% (e) (i) LiOH.H₂O.H₂O₂, THF/H₂O, rt 4 hr., (ii) DIPCDI, HOAt, DMF, 40° C., 20 hr. 37% for 2 steps (f) 2$^{nd}$ Grubbs, CH₂Cl₂, 60-66° C. for 18 hours (g) TFA/H₂O/EDT, 46% (h) TFA/DCM, quantitative.
Figure 6A:
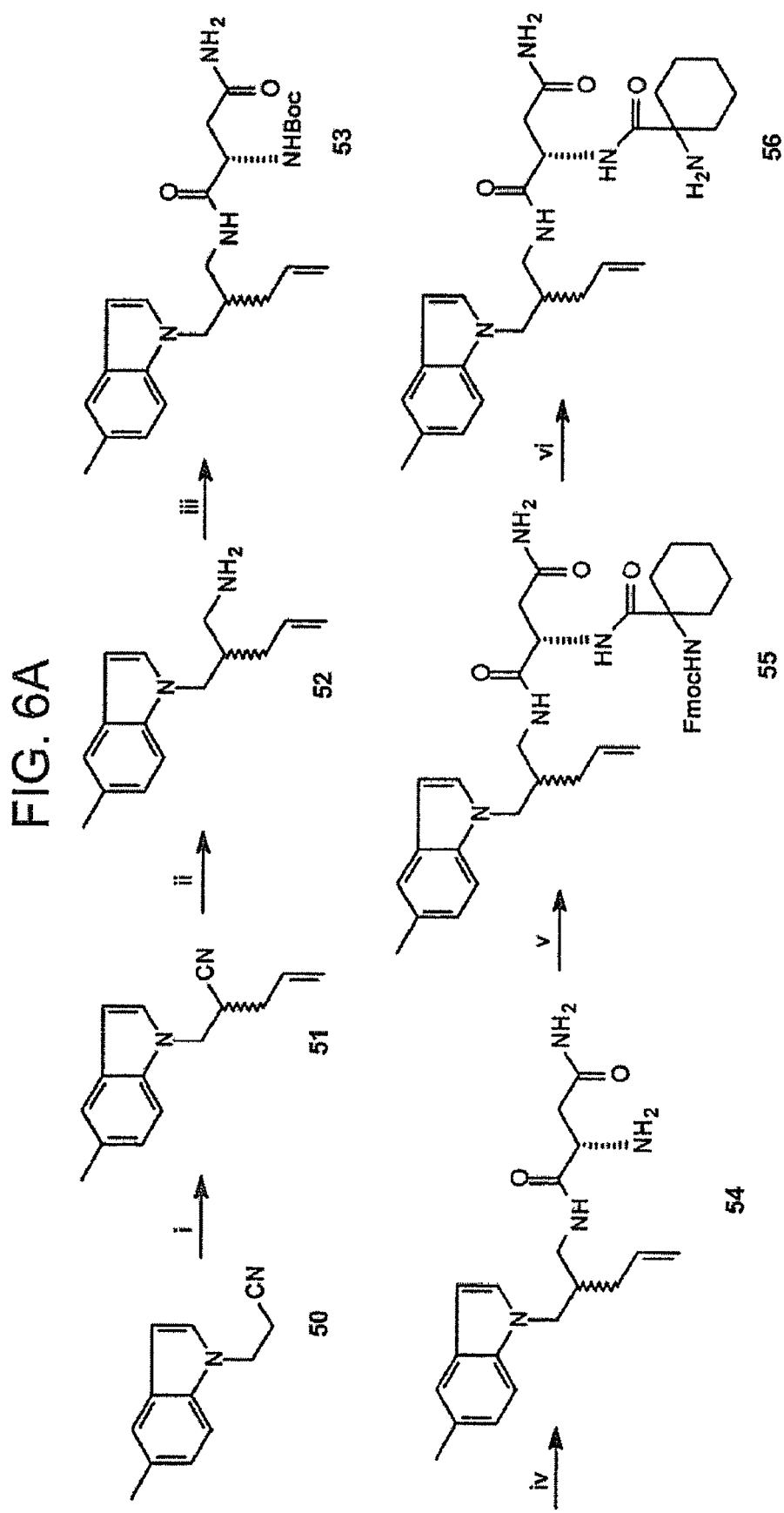
FIG. 6A depicts a method of preparing compound 56, which is an intermediate in preparing compound 61 of the present invention. Reagents and conditions: (i) LDA, allyl bromide, THF, −78° C., 2 h (41% yield); (ii) LiAlH₄, THF, 25° C., 12 h (39% yield); (iii) Boc-Asn-OH, DIPCDI, HOBt, DMF, rt, 10 h; (iv) HCl$_{(aq)}$ (2N), CH₃CN, rt, 15 h; (v) N-Fmoc Ac₆c, EDCI.HCl, HOBt, DMF, rt, 12 h, (65% yield in three steps); (vi) piperidine, CH₃CN, rt, 2 h, (85% yield).
Figure 6B:
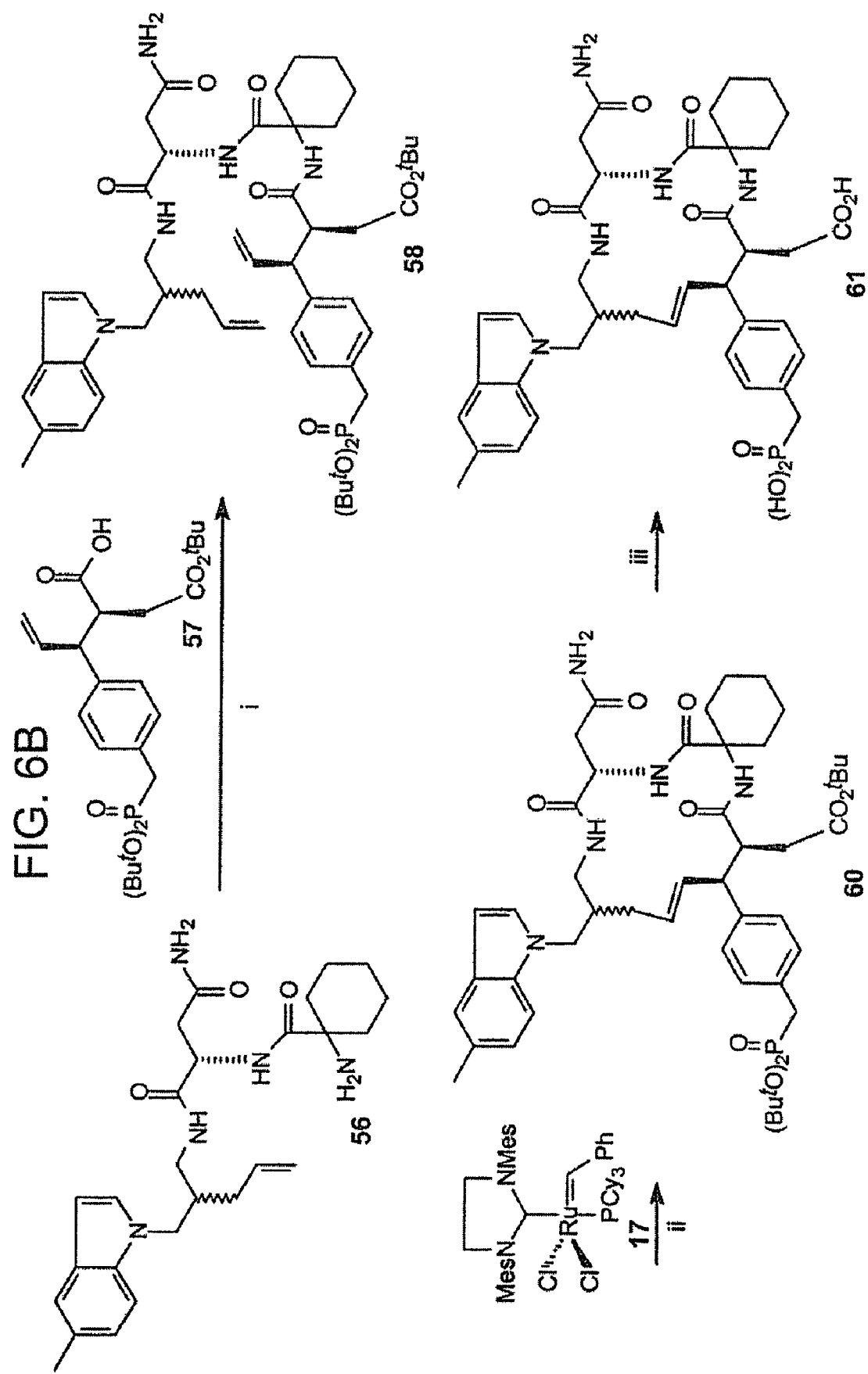
FIG. 6B depicts a method of preparing compound 61 of the present invention. Reagents and conditions: (i) EDCI.HCl, HOAt, DMF, 50° C., 24 h (12% yield); (ii) [((Pcy₃)(Im (Mes)₂) Ru═CHPh)], CH₂Cl₂, reflux, 48 h (49% yield); (iii) TFA-HS(CH₂)₂SH—H₂O, rt, 1 h (26% yield).

The compounds of the present invention can be prepared by any suitable method. For example, compounds 5-6 can be prepared as shown in FIGS. 1A and 1B. Compound 28 can be prepared as shown in FIG. 2. Compounds 32-33 can be prepared as shown in FIG. 3. Compound 41 can be prepared as shown in FIG. 4. Compound 49 can be prepared as shown in FIG. 5. Compound 61, which is a mixture of the two stereoisomers, can be prepared as shown in FIGS. 6A and 6B. Compound 62 can be obtained by separating the desired isomer from compound 60.

In accordance with an embodiment, the present invention provides compound of formula I or a pharmaceutically acceptable salt thereof. As used herein, the term "pharmaceutically acceptable salt" refers to a salt prepared from pharmaceutically acceptable non-toxic organic or inorganic bases. Suitable inorganic bases include, but are not limited to, alkaline and earth-alkaline metals such as aluminum, calcium, lithium, magnesium, potassium, sodium and zinc. The salt can be mono, di, tri, or higher.

The present invention further provides a pharmaceutical composition comprising a compound of the invention and a pharmaceutically acceptable carrier. Thus, for example, the present invention provides a composition comprising a pharmaceutically acceptable carrier and an effective (e.g., therapeutically or prophylactically effective) amount of at least one of the compounds set forth above. The present invention further provides a method of inhibiting an SH2 domain from binding with a phosphoprotein comprising contacting a sample or substance containing an SH2 domain with a compound of the present invention.

The present invention discloses the use of above compounds in the manufacture of a medicament for the treatment of a condition that responds to the inhibition of phosphoprotein binding to an SH2 domain of a mammal. The present invention further teaches the use of the above compounds in medicine. The compounds find use as a Grb2 SH2 domain binding inhibitor, i.e., for inhibiting binding with a phosphoprotein.

The pharmaceutically acceptable (e.g., pharmacologically acceptable) carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can comprise (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants. The quantity of surfactant in such formulations typically ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate. Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of responses. Typically the dosages range from about 0.001 to about 1000 mg/kg body weight of the animal being treated/day. Preferred dosages range from about 0.01 to about 10 mg/kg body weight/day, and further preferred dosages range from about 0.01 to about 1 mg/kg body weight/day.

Embodiments of the compounds have the advantage that they are stable to or in presence of enzymes encountered during in vivo use. Embodiments of the compounds can find use in in vitro and in vivo applications. For example, the compounds can find use as molecular probes as well as in assays to identify, isolate, and/or quantitate receptor or binding sites in a cell or tissue. The compounds also can find use in vivo for studying the efficacy in the treatment of various diseases or conditions involving SH2 domains.

The present invention further provides a method of preventing or treating a disease, state, or condition, which is mediated by the binding of an SH2 domain-containing protein with a phosphoprotein, in a mammal by the use of the compounds of the present invention. In an embodiment, the method involves preventing a disease, state, or condition. In another embodiment, the method involves treating an existing disease, state, or condition.

Preferably, the method involves inhibition of SH2 domain binding with a phosphoprotein. The SH2 domain may involve one or more of the following proteins: Src, Lck, Eps, ras GTPase-activating protein (GAP), phospholipase C, phosphoinositol-3 (P1-3)kinase, Fyn, Lyk, Fgr, Fes, ZAP-70, Sem-5, p85, SHPTP1, SHPTP2, corkscrew, Syk, Lyn, Yes, Hck, Dsrc, Tec, Atk/Bpk, Itk/Tsk, Arg, Csk, tensin, Vav, Emt, Grb2, BCR-Abl, Shc, Nck, Crk, CrkL, Syp, Blk, 113TF, 91TF, Tyk2, especially Src, phospholipase c, phosphoinositol-3 (p1-3)kinase, Grb2, BCR-Abl, Shc, Nck, Crk, CrkL, Syp, Blk, 113TF, 91TF, and Tyk2.

The method comprises administering to the mammal one or more compounds of the present invention. The disease, state, condition can be a cancer, e.g., a breast cancer or an ovarian cancer, or a tumor such as a solid tumor, e.g., a brain tumor, a prostate tumor, and the like, leukemia including chronic myelocytic leukemia, lymphoma, an autoimmune disease, an inflammatory disease, a metabolic disease, diabetes, obesity, or cardiovascular disease.

The present invention further provides a method of enhancing the therapeutic effect of a treatment rendered to a mammal comprising administering a compound in conjunction with the treatment. By conjunction, it is meant that the inhibitor can be used in any suitable manner, for example, prior to, simultaneously with, or post-administration of the therapeutic agent. Synergistic effects are observed when the SH2 domain binding inhibitor is used in combination with other treatments known to those skilled in the art. The inhibitor enhances the cytotoxicity of the chemotherapeutic treatments. Cancer treatment is particularly suitable for this combination treatment.

The cancer may involve any number of mechanisms. A majority of human breast cancer is dependent upon activation of the Ras signaling pathways through activation of growth factor receptor as the means to achieve continuous cellular proliferation. For example, the cancer may involve overexpression of Her-2/neu. The cancer can be mediated through BCR-Abl or the expression of erbB-2 receptor. In cells transformed by p185 erbB-2 overexpression, therapeutic agents affecting Grb2 function at its SH2 domain may interrupt the flow of signal transduction to the ras pathway and thus result in reversal of the cancer phenotype.

The compounds of the present invention interact with intracellular signal transducers, thus interfering in the pathways leading to cell proliferation and movement. These biological effects can be utilized to inhibit growth of neoplastic cells, inhibit angiogenesis, and to prevent metastatic spreading. The present invention provides a method for preventing or treating a disease, condition, or state in a mammal that is mediated by the binding of an intracellular signal transducer to a receptor protein tyrosine kinase comprising administering to the mammal a peptide of the present invention.

The compounds of the present invention are of use in medicine, e.g., in the manufacture of a medicament for the treatment of a condition that responds to the inhibition of phosphoprotein binding to an SH2 domain of a mammal.

The present invention further provides a method for determining the presence of an SH2 domain in a material comprising (a) exposing a sample of said binding material to a SH2 binding compound and obtaining a first binding result; (b) exposing another sample of said material to a compound described above and obtaining a second binding result; and (c) comparing the first and second binding results to determine whether an SH2 domain is present in the material.

The present invention further provides a method for inhibiting an SH2 domain from binding with a phosphoprotein comprising contacting an SH2 domain with a compound of the invention. The present invention further provides a method for inhibiting the binding of an intracellular transducer to a receptor protein tyrosine kinase comprising contacting (a) a sample containing the receptor protein tyrosine kinase, (b) the intracellular transducer, and (c) a compound of the present invention under conditions wherein, in the absence of the compound, the receptor protein tyrosine kinase binds to the intracellular transducer; wherein the contacting results in the inhibition of binding of the intracellular transducer to the receptor protein tyrosine kinase.

The present invention further provides for detecting the inhibition of binding of an intracellular transducer to a receptor protein tyrosine kinase comprising: (a) contacting a sample containing the receptor protein tyrosine kinase with the intracellular transducer, separately, in the presence and absence of the compound of the present invention under conditions that allow for binding of the receptor protein tyrosine kinase to the intracellular transducer in the absence of the compound; (b) determining that binding has occurred between the receptor protein tyrosine kinase and the intracellular transducer; and (c) comparing the relative binding levels of the receptor protein tyrosine kinase to the intracellular transducer in the presence and absence of the compound.

The following examples further illustrate the invention but, of course, should not be construed as in any way limiting its scope.

EXAMPLE 1

This Example illustrates methods of preparing compounds in accordance with an embodiment of the present invention. The methods are illustrated schematically in FIGS. 1-6.

Compounds 5-6 are prepared as shown in FIG. 1A-B.

(4S)-3-[3-(5-methylindolyl)propanoyl]-4-phenyl-1,3-oxazolidin-2-one (8). To the suspension of (4S)-4-phenyl-1,3-oxazolidin-2-one (6.85 g, 42 mmol) in anhydrous THF (130 mL) was added BuLi (26.3 mL, 42 mmol) at −78° C. and the mixture was stirred under argon (0.5 h). To the above suspension was added a solution of active ester prepared by reacting 3-(5-methylindolyl)propanoic acid 7 (10.23 g, 50.39 mmol) in anhydrous THF (130 mL) and trimethylacetyl chloride (5.10 g, 50.39 mmol) in the presence of N-methyl morphine (6.06 g, 50.39 mmol) at 0° C. under argon, followed by stirring at −78° C. (1 h). The combined reaction mixture was stirred at −78° C. for an additional 2 h, then the solution was warmed to room temperature and stirred overnight. The reaction was quenched by the addition of ice-cold saturated $NH_4Cl$ solution (120 mL), extracted with EtOAc, washed with brine and dried ($Na_2SO_4$). Evaporation provided a residue, which was purified by silica gel flash chromatography to provide 8 as colorless oil. (12.7 g, 87% yield). $^1$H NMR ($d_6$-DMSO) δ 7.36-7.23 (m, 8H), 6.94 (dd, 1H, J=1.5 Hz & 8.5 Hz), 6.28 (dd, 1H, J=0.8 Hz & 3.1 Hz), 5.43: (dd, 1H, J=3.5 Hz & 8.6 Hz), 4.70 (t, 1H, J=8.8), 4.40 (s, 1H), 4.40-4.37 (m, 2H), 4.15 (dd, 1H, J=3.5 Hz & 8.8 Hz), 3.41-3.30 (m, 2H), 2.36 (s, 3H). FABMS (+Ve) m/z 348 [M+], 349 [MH$^+$]. Anal. Calcd for $C_{21}H_{20}N_2O_3$ C, 72.40; H, 5.79; N, 8.04. Found C, 72.33; H, 5.77; N, 8.15.

(4S)-3-{(2S)-2-[(5-methylindolyl)methyl]pent-4-enoyl}-4-phenyl-1,3-oxazolidin-2-one (9). To a stirred solution of NaHMDS 1 M in THF (36.40 mL, 36.40 mmol) was added dropwise a solution of 8 (11.51 g, 33.04 mmol) in THF (180 mL) at −78° C. under argon. The solution was stirred at −78° C. (2 h), then allyl iodide (6.66 g, 39.65 mmol) in THF (70 mL) was added and the mixture was stirred for an additional 2 h at −78° C. The reaction mixture was warmed to room temperature and stirred overnight. The reaction was quenched by the addition of ice-cold saturated $NH_4Cl$ solution (200 mL), extracted with EtOAc, washed with brine and dried ($Na_2SO_4$). Evaporation provided a residue, which was purified by silica gel flash chromatography to provide 9 as colorless oil. (7.82 g, 61% yield). H NMR ($d_6$-DMSO) δ 7.37-7.21 (m, 8H), 6.97 (dd, 1H, J=1.5 Hz & 8.5 Hz), 6.31 (dd, 1H, J=0.8 Hz & 3.1 Hz), 5.56 (m, 1H), 5.34 (dd, 1H, J=3.8 Hz & 8.5 Hz), 4.94-4.90 (m, 2H), 4.50 (t, 1H, J=8.7), 4.46-4.38 (m, 2H), 4.17 (m, 1H), 4.11 (dd, 1H, J=3.5 Hz & 8.8 Hz), 2.37 (s, 3H), 2.32 (m, 1H), 2.17 (m, 1H). FABMS (+Ve) m/z 388 [M+], 389 [MH$^+$]. Anal. Calcd for $C_{24}H_{24}N_2O_3$ C, 74.21; H, 6.23; N, 7.21. Found C, 74.29; H, 6.22; N, 7.20.

(2S)-2-[(5-methylindolyl)methyl]pent-4-en-1-ol (10). To a stirred suspension of $LiAlH_4$ (718 mg, 17.90 mmol) in THF (60 mL) was added a precooled solution of 8 (5.78 g, 14.9 mmol) in THF (50 mL) at −78° C. under argon. The mixture was stirred at −78° C. (1 h), then raised to 0° C. (1 h). After an additional 3 h at 0° C., the reaction mixture was cooled to −78° C. and EtOAc (20 mL) was added followed by 10% NaOH (aq) (30 drops). The reaction was quenched by the addition of ice-cold saturated $NH_4Cl$ solution (150 mL), extracted with $Et_2O$, washed with brine and dried ($Na_2SO_4$).

Evaporation provided a residue, which was purified by silica gel flash chromatography to yielded 10 as colorless oil. (3.14 g, 92% yield). H NMR (d$_6$-DMSO) δ 7.32-7.30 (m, 2H), 7.25 (d, 1H, J=2.9 Hz), 6.94 (dd, 1H, J=1.3 Hz & 8.5 Hz), 6.31 (d, 1H, J=0.8 Hz & 3.1 Hz), 5.78 (m, 1H), 5.04-4.98 (m, 2H), 4.63 (t, 1H, J=5.0), 4.16 (dd, 1H, J=6.9 Hz & 14.2 Hz), 4.02 (dd, 1H, J=6.3 Hz & 14.2 Hz), 3.30-3.23 (m, 2H), 2.36 (s, 3H), 2.09-1.92 (m, 3H). FABMS (+Ve) m/z 229 [M+], 230 [MH$^+$]. Anal. Calcd for C$_{15}$H$_{19}$NO C, 78.56; H, 8.35; N, 6.11. Found C, 78.47; H, 8.50; N, 6.16.

2-{(2R)-2-[(5-methylindolyl)methyl]pent-4-enyl}-2-hydrocyclopenta[1,2-a]benzene-1,3-dione (11). Diisopropyl azodicarboxylate (1.51 g, 7.50 mmol) was added to a solution of 10 (1.14 g, 4.98 mmol), phthalimide (1.11 g, 7.50 mmol) and triphenylphosphine (2.03 g, 7.50 mmol) in THF (40 mL) at 0° C. The mixture was stirred at room temperature for 12 h. The solvent was removed and the residue was purified by silica gel flash chromatography to provide 11 as colorless oil. (1.57 g, 88% yield). H NMR (d$_6$-DMSO) δ 7.84-7.81 (m, 4H), 7.34-7.27 (m, 3H), 6.92 (dd, 1H, J=1.3 Hz & 8.3 Hz), 6.30 (dd, 1H, J=0.8 Hz & 2.9 Hz), 5.74 (m, 1H), 5.02-4.93 (m, 2H), 4.17 (dd, 1H, J=7.0 Hz & 14.2 Hz), 4.10 (dd, 1H, J=7.4 Hz & 14.4 Hz), 3.64 (dd, 1H, J=7.5 Hz & 13.9 Hz), 3.44 (dd, 1H, J=6.6 Hz & 13.9 Hz), 2.53 (m, 1H), 2.35 (s, 3H), 2.03-1.91 (m, 2H). FABMS (+Ve) m/z 358 [M+], 359 [MH$^+$]. Anal. Calcd for C$_{23}$H$_{22}$N$_2$O$_2$ C, 77.07; H, 6.19; N, 7.82. Found C, 76.78; H, 6.31; N, 7.69.

(2R)-2-[(5-methylindolyl)methyl]pent-4-enylamine (12). To a stirred solution of 11 (3.36 g, 9.37 mmol) in EtOH (70 mL) containing H$_2$O (688 mg) was added hydrazine (1.13 g, 22.5 mmol). The resulting solution was refluxed under argon for 3 h, during which time a significant quantity of solid precipitated. The mixture was filtered through celite, washed with EtOH and the combined filtrate was evaporated and the residue was purified by silica gel flash chromatography to provide 3 as colorless oil. (1.79 g, 84% yield). H NMR (d$_6$-DMSO) δ 7.34-7.27 (m, 3H), 6.93 (d, 1H, J=8.4 Hz), 6.31 (d, 1H, J=3.1 Hz), 5.77 (m, 1H), 5.06-4.99 (m, 2H), 4.16 (dd, 1H, J=6.6 Hz & 14.3 Hz), 3.99 (dd, 1H, J=6.4 Hz & 14.3 Hz), 2.42 (t, 2H, J=4.5 Hz), 2.36 (s, 3H), 2.05 (m, 1 H), 1.98-1.90 (m, 2H). FABMS (+Ve) m/z 229 [MH$^+$]. Anal. Calcd for C$_{15}$H$_{20}$N$_2$O.0.25 H$_2$O C, 77.42; H, 8.82; N, 12.04. Found C, 77.72; H, 9.03; N, 11.89.

N-{(2R)-2-[(5-methylindolyl)methyl]pent-4-enyl}(2S)-2-amino-3-carbamoylpropanamide (13). To a solution of 12 (436 mg, 1.91 mmol) in DMF (9 mL) was added an active ester solution prepared by the reaction of Boc-Asn-OH (466 mg, 2.00 mmol), HOBt (270 mg, 2.00 mmol) and DIPCDI (252 mg, 2.00 mmol) in DMF (6 mL) at room temperature for 10 min). The resulting solution was stirred at room temperature for 12 h. The solvent was evaporated and the residue was dissolved in EtOAc, washed with water, brine, dried over Na$_2$SO$_4$ and evaporated to provide crude N-Boc protected 12 (791 mg). To a solution of this material (791 mg, 1.79 mmol) in CH$_3$CN (20 mL) was added 2 N HCl$_{aq}$ (20 mL) and the resulting solution was stirred at room temperature for 12 h. After neutralization with saturated NaHCO$_{3aq}$ and evaporation of organic solvent, the mixture was extracted with EtOAc, washed with H$_2$O, brine, and dried over Na$_2$SO$_4$. The solvent was removed and the residue was purified by silica gel flash chromatography to provide 13 as colorless oil (491 mg, 75% yield). H NMR (d$_6$-DMSO) δ 7.96 (t, 1 H, J=5.6 Hz), 7.40 (s, 1H), 7.33-7.30 (m, 3H), 6.95 (dd, 1H, J=1.2 Hz & 8.4 Hz), 6.32 (dd, 1H, J=0.6 Hz & 2.8 Hz), 5.77 (m, 1H), 5.06-5.00 (m, 2H), 4.09 (dd, 1H, J=7.2 Hz & 14.4 Hz), 3.98 (m, 1H), 3.49 (dd, 1H, J=4.4 Hz & 8.4 Hz), 3.11 (m, 1H), 2.97 (m, 1H), 2.42 (dd, 1H, J=4.4 Hz & 15.2 Hz), 2.36 (s, 3H), 2.24 (dd, 1H, J=8.4 Hz & 14.8 Hz), 2.15 (dd, 1H, J=6.4 Hz & 12.8 Hz), 1.99 (dd, 1H, J=6.8 Hz & 14.4 Hz), 1.91 (m, 1 H). FABMS (+Ve) m/z 343 [MH$^+$], 365 [MNa$^+$]. Anal. Calcd for C$_{19}$H$_{26}$N$_4$O$_2$.1.25 H$_2$O C, 62.55; H, 7.82; N, 15.36. Found C, 63.06; H, 8.11; N, 14.93.

N-{(2R)-2-[(5-methylindolyl)methyl]pent-4-enyl}(2S)-3-carbamoyl-2-({[(fluoren-9-ylmethoxy)carbonylamino] cyclohexyl}carbonylamino)propanamide(N-Fmoc 14). To a solution of 13 (471 mg, 1.38 mmol) and Fmoc-1-amino-cyclohexenecarboxylic acid (504 mg, 1.38 mmol) in DMF (10 mL) was added HOBt (205 mg, 1.52 mmol) and EDCI.HCl (291 mg, 1.52 mmol) at 0° C. The mixture was stirred at room temperature for 12 h. After removal of solvent, the residue was dissolved in EtOAc (100 mL), washed with 5% citric acid, 5% NaHO$_3$ and brine, dried over Na$_2$SO$_4$. The solvent was removed and the residue was purified by silica gel flash chromatography to provide N-Fmoc-protected 14 as colorless oil. (789 mg, 83% yield). H NMR (d$_6$-DMSO) δ 8.10 (d, 1 H, J=2.0 Hz), 7.90-7.61 (m, 5 H), 7.49 (t, 1H, J=7.6 Hz), 7.42-7.21 (m, 8H), 6.90 (s, 1 H), 6.82 (d, 1H, J=8.8 Hz), 5.63 (m, 1H), 4.94-4.86 (m, 2H), 4.41 (m, 1H), 4.29 (dd, 1H, J=10.0 Hz & 12.5 Hz), 4.22-4.17 (m, 2H), 4.06 (dd, 1H, J=6.3 Hz & 14.3 Hz), 3.90 (dd, 1H, J=7.6 Hz & 14.4 Hz), 3.02 (m, 1H), 2.90 (m, 1H), 2.66 (dd, 1H, J=6.9 Hz & 15.4 Hz), 2.52 (dd, 1H, J=5.2 Hz & 15.2 Hz), 2.32 (s, 3H), 2.07 (m, 1H), 1.95-1.19 (m, 12 H). FABMS (+Ve) m/z 690 [MH$^+$]. Anal. Calcd for C$_{41}$H$_{47}$N$_5$O$_5$.2H$_2$O C, 67.84; H, 7.08; N, 9.65. Found C, 67.98; H, 6.86; N, 10.01.

N-{(2R)-2-[(5-dimethylindolyl)methyl]pent-4-enyl}(2S)-2-aminocyclohexyl) carbonylamino)]3-carbamoylpropanamide (14). To a solution of N-Fmoc-protected 14 (763 mg, 1.11 mmol) in CH$_3$CN (12 mL) was added piperidine (1.2 mL) and the resulting solution was stirred at room temperature for 1.5 h. Evaporation of solvent gave a residue, which was purified by silica gel flash chromatography to provide 14 as colorless oil. (446 mg, 86%). H NMR (d$_6$-DMSO) δ 8.46 (s, 1H), 7.79 (t, 1 H, J=5.9 Hz), 7.38-7.29 (m, 5H), 6.94 (dd, 1H, J=1.5 Hz & 8.5 Hz), 6.89 (s, 1 H), 6.31 (d, 1H, J=3.1 Hz), 5.73 (m, 1H), 5.04-4.98 (m, 2H), 4.44 (t, 1H, J=6.1 Hz), 4.08 (dd, 1H, J=6.4 Hz & 14.4 Hz), 3.95 (dd, 1H, J=7.7 Hz & 14.4 Hz), 3.14 (dd, 1H, J=5.9 Hz & 13.5 Hz), 2.91 (dd, 1H, J=6.8 Hz & 13.5 Hz) 2.55 (dd, 1H, J=6.4 Hz & 15.2 Hz), 2.42 (dd, 1H, J=6.1 Hz & 15.2 Hz), 2.36 (s, 3H), 2.11 (m, 1H), 1.99-1.84 (m, 2H), 1.77-1.13 (m, 10H). FABMS (+Ve) m/z 468 [MH$^+$]. Anal. Calcd for C$_{26}$H$_{37}$N$_5$O$_3$.0.5H$_2$O C, 65.54; H, 7.98; N, 14.71; Found C, 65.74; H, 8.00; N, 14.73.

Tert-butyl 3-[N-({N-[1-N-{(2R)-2-[(5-methylindolyl)methyl]pent-4-enyl}carbamoyl)(1S)-2-carbamoylethyl] carbamoyl}cyclohexyl)carbamoyl)] (3S,4S)-4-(4-{[bis(tert-butoxy)phosphono]methyl}phenyl)hept-6-enoate (16). To a solution of 14 (100 mg, 0.210 mmol) and compound 15 (133 mg, 0.278 mmol) in DMF (4 mL) was added HOAt (0.630 mL, 0.315 mmol) and EDCI.HCl (61 mg, 0.315 mmol) at 0° C. The solution was stirred at room temperature (1.5 h) then heated to 50° C. and stirred (24 h). The crude reaction mixture was evaporated in vacuo and residue was purified by silica gel flash chromatography to provide 16 as colorless oil. (111 mg, 56% yield). H NMR (d$_6$-DMSO) δ 8.21 (s, 1H), 7.46 (d, 1H, J=7.4 Hz), 7.38-7.33 (m, 5H), 7.15-7.12 (m, 4H), 6.93 (dd, 1H, J=1.3 Hz & 8.2 Hz), 6.83 (s, 1 H), 6.32 (dd, 1H, J=2.9 Hz & 9.0 Hz), 5.79 (m, 1H), 5.67 (ddd, 1H, J=7.1 Hz & 9.7 Hz & 16.8 Hz) 5.08-4.94 (m, 4H), 4.78 (dd, 1H, J=2.0 Hz & 10.0 Hz), 4.21 (m, 1H), 4.12 (dd, 1H, J=6.9 Hz & 14.4 Hz), 4.02 (m, 1H), 3.50 (t, 1H, J=8.6 Hz), 3.24 (m, 1H), 3.03 (dd, 1H, J=6.7 Hz & 13.2 Hz), 2.93 (d, 2H, J=21.1 Hz), 2.91 (m, 1H, J=7.1 Hz & 13.7 Hz), 2.61-2.50 (m, 3H), 2.38 (s, 3H), 2.24 (m, 1H), 2.12 (dd, 1H, J=4.3 Hz & 17.0 Hz), 2.03 (m, 1H), 1.87 (m, 1H), 1.72-1.02 (m, 10H), 1.35 (s, 18H), 1.33 (s, 9H). FABMS (+Ve) m/z 946 [MH$^+$]. Anal. Calcd for $C_{56}H_{76}N_5O_9P\cdot 2H_2O$ C, 63.58; H, 8.21; N, 7.13. Found C, 63.89; H, 8.51; N, 5.65.

Tert-butyl 2-[(9S,10S,18S,14R)-7,16,19-triaza-10-(4-{[bis(tert-butoxy) phosphono]methyl}phenyl)-18-(carbamoylmethyl)-14-[(5-methylindolyl)methyl]-8,17, 20-trioxospiro[5.14]icos-11-en-9-yl]acetate (18). To a solution of 16 (60 mg, 0.063 mmol) in $CH_2Cl_2$ (15 mL) was added ruthenium catalyst 17 (27 mg, 0.032 mmol) in $CH_2Cl_2$ (5 mL) under argon. The reaction mixture was stirred at 45° C. (48 h). The crude reaction mixture was evaporated in vacuo, and residue was purified by silica gel flash chromatography to give 18 as yellow oil. (41 mg, 70%). H NMR ($d_6$-DMSO) δ 8.67 (s, 1H), 8.48 (d, 1H, J=7.8 Hz), 8.00 (brs, 1H), 7.57 (t, 1H, J=5.5 Hz), 7.34-7.10 (m, 8H), 6.93 (dd, 1H, J=1.4 Hz & 8.4 Hz), 6.27 (d, 1H, J=2.9 Hz), 5.81 (dd, 1H, J=10.4 Hz & 14.9 Hz), 5.44 (dt, 1H, J=6.8 Hz & 15.2 Hz), 4.48 (t, 1H, J=4.5 Hz), 4.22 (dd, 1H, J=5.1 Hz & 13.9 Hz), 4.06 (m, 1H), 3.82 (dd, 1H, J=9.8 Hz & 14.3 Hz), 3.57 (dd, 1H, J=6.3 Hz & 12.7 Hz), 3.38 (m, 1H), 3.02 (dd, 1H, J=4.3 Hz & 10.5 Hz), 3.00 (d, 2H, J=21.3 Hz), 2.97 (dd, 1H, J=6.1 Hz & 9.0 Hz), 2.82-2.68 (m, 3H), 2.45 (dd, 1H, J=4.9 Hz & 15.2 Hz), 2.35 (s, 3H), 2.10-1.88 (m, 3H), 1.85-1.48 (m, 10 H), 1.36 (s, 18H), 1.30 (s, 9H). FABMS (+Ve) m/z 918 [MH$^+$].

2-{(9S,10S,14R,18S)-7,16,19-Triaza-18-(carbamoylmethyl)-14-[(5-methyl indolyl)methyl]-8,17,20-trioxo-10-[4-(phosphonomethyl)phenyl]spiro[5.14]icos-11-en-9-yl}acetic acid (5). A solution of 18 (18 mg, 0.0196 mmol) in a mixture of TFA-ethanedithol-$H_2O$ (1.0 mL, v:v, 3.8:0.1:0.1) was stirred at room temperature (1 h). The mixture was reduced under vacuum to a volume of 0.25 mL. Diethyl ether (5 mL) was added giving a purple solid. The solid was collected and purified by HPLC as follows: A linear gradient over 25 minutes of from 0.1% TFA in 5% $CH_3CN$: 95% $H_2O$ to 0.1% TFA in 95% $CH_3CN$: 5% $H_2O$; analytical retention time=28.5 min; preparative retention time=16.9 min. Lyophilization provided 5 as a pale solid (5.2 mg, 35% yield) in 98% purity as determined by HPLC. H NMR ($d_6$-DMSO) δ 8.52 (s, 1H), 8.27 (d, 1H, J=8.0 Hz), 7.54 (brs, 1H), 7.36 (d, 1H, J=8.4 Hz), 7.30-7.08 (m, 7H), 6.94 (d, 1H, J=7.0 Hz), 6.52 (brs, 1H), 6.31 (d, 1H, J=3.1 Hz), 5.74 (dd, 1H, J=11.3 Hz & 14.7 Hz), 5.47 (m, 1H), 4.28 (m, 1H), 4.19 (d, 1H, J=6.4 Hz & 14.4 Hz), 4.06 (m, 1H), 3.93 (dd, 1H, J=7.8 Hz & 14.1 Hz), 3.42 (m, 1H), 3.17 (m, 1H), 2.89 (d, 2H, J=21.5 Hz), 2.84 (dd, 1H, J=4.8 Hz & 15.2 Hz), 2.72 (m, 1H), 2.36 (s, 3H), 2.31 (m, 1H), 2.20 (m, 1H), 2.00-1.91 (m, 3H), 1.88-1.72 (m, 3H), 1.57-1.40 (m, 4H), 1.31-1.14 (m, 3H). FABMS (+Ve) m/z 748 [M−H], 770 [M−2H+Na].

Conversion of 5 to the tri-sodium salt (6). To a solution of 5 (3.2 mg, 0.00426 mmol) in $CH_3CN$:$H_2O$ (1.0 mL, v/v=1:1) at room temperature was added a solution of $NaHCO_3$ (0.0128 mmol) in $H_2O$ (0.364 mL) and the resulting mixture was lyophilized to provided 6 as a pale solid (3.5 mg, 100% yield).

Compound 28 of the invention can be prepared as shown in FIG. 2.

Preparation of compound 20. To a stirred suspension of NaH (60% in mineral oil, 6.3 g, 157 mmol) in diethyl ether 800 mL was added trimethyl phosphonoacetate (26 g, 143 mmol) in diethyl ether 200 mL slowly at 0° C. and the mixture was stirred for 20 min. at 0° C. 4-nitrobenzaldehyde (21.6 g, 143 mmol) was added in small portions. The mixture was stirred overnight at room temperature. The mixture was extracted by ethyl acetate (EA)/$H_2O$ and EA was collected to be dried by $MgSO_4$. Evaporation and washing with ether 20 mL of formed solid gave 20 (22.5 g, 86%) as pale yellow solid. Mp 159-160° C. $^1$H NMR ($CDCl_3$) 8.25 (2 H, m), 7.72 (1 H, d, J=16.2 Hz), 7.67 (2 H, m), 6.56 (1 H, d, J=16.0 Hz), 3.84 (3 H, s). FAB-MS (+VE) m/z 208 (MH$^+$). Anal. Calcd. For $C_9H_7NO_4$: C, 57.97; H, 4.38; N, 6.76. Found: C, 58.06; H, 4.40; N, 6.75

Preparation of compound 21. To a stirred suspension of 20 (22 g, 106 mmol) in $H_2O$/THF/MeOH=200 mL/200 mL/100 mL mixture was added $LiOH\cdot H_2O$ (13.4 g, 318 mmol) and the whole mixture was stirred for 2.5 hours at room temperature. The mixture was neutralized by 1 N HCl (320 mL, 320 mmol) to be carefully extracted by EA. The combined organic layer was dried by $MgSO_4$. Evaporation and washing with ether 30 mL of formed solid gave intermediate acid as crystalline solid (18.8 g, 92%) as pale yellow solid. (Mp 245° C. decomposition. $^1$H NMR (DMSO-$d_6$) δ 12.69 (1 H, s), 8.24 (2 H, m), 7.98 (2 H, m), 7.70 (1 H, d, J=16.0 Hz), 6.75 (1 H, d, J=16.0 Hz). FAB-MS (−VE) m/z 192 (M−H). Anal. Calcd. For $C_9H_7NO_4\cdot 0.25H_2O$: C, 54.69; H, 3.82; N, 7.09. Found: C, 54.55; H, 3.58; N, 7.03). To this stirred suspension of intermediate acid (18.7 g, 97 mmol) in anhydrous THF 500 mL was added N-methyl morpholine (11.2 mL, 102 mmol) and then was added trimethylacetyl chloride (12.5 mL, 102 mmol) at 0° C. The mixture was stirred for 30 minutes at room temperature. Meanwhile n-BuLi (1.6 Mol. In hexanes, 63.8 mL, 102 mmol) was added to the stirred solution of S-(+)-4-phenyl-2-oxazolidinone (5.8 g, 97 mmol) in THF 500 mL slowly at −78° C. The mixture was stirred for 30 minutes at −78° C. and the above mixture was added to this oxazolidinone-Li salt via cannula at −78° C. slowly. The cooling bath was removed and the whole mixture was stirred for 2 hours at room temperature. The mixture was extracted by Ethyl acetate/$H_2O$ and the organic layer was collected to be dried by $MgSO_4$. Evaporation and washing with ether 15 mL of formed solid gave 21 (26.6 g, 81%) as yellow solid. Mp 177-179° C. $^1$H NMR ($CDCl_3$) δ 8.24 (2 H, m), 8.04 (1 H, d, J=15.8 Hz), 7.79-7.71 (3 H, m), 7.44-7.34 (5 H, m), 5.56 (1 H, dd, J=3.9 and 8.8 Hz), 4.78 (1 H, t, J=8.8 Hz), 4.36 (1 H, dd, J=3.9 and 9.0 Hz). FAB-MS (+VE) m/z 339 (MH$^+$). Anal. Calcd. For $C_{18}H_{14}N_2O_5$: C, 63.90; H, 4.17; N, 8.28. Found: C, 63.87; H, 4.29; N, 8.23.

Preparation of compound 22. To a stirred suspension of PhSCu (9.8 g, 56.8 mmol) in anhydrous diethyl ether 800 mL was added vinylmagnesium bromide (1 Mol. In THF, 142 mL, 142 mmol) slowly at −48~−45° C. and was stirred for 25 minutes at −20° C. The mixture was cooled to −45° C. again and the pre-cooled (to −10° C.) solution of 21 (16 g, 47.3 mmol) in THF/$CH_2Cl_2$=60 mL/100 mL was added dropwise at −45° C. via cannular. The mixture was stirred for 15 minutes at −35° C. and was poured into the $NH_4Cl$ aq. Solution. Careful extraction by EA and the collected organic phase was dried by $MgSO_4$. Evaporation and purification by column chromatography gave 22 (3.98 g, 23%) as yellow oil, recovering starting material 21 (6.88 g, 43%). $^1$H NMR ($CDCl_3$) δ 8.11 (2 H, m), 7.39-7.32 (5 H, m), 7.25 (2 H, m), 5.94 (1 H, m), 5.33 (1 H, dd, J=3.5 and 8.6 Hz), 5.10-4.98 (2 H, m), 4.64 (1 H, t, J=9.0 Hz), 4.28 (1 H, dd, J=3.7 and 9.0 Hz). 4.02 (1 H, m), 3.46 (2 H, m). FAB-MS (+VE) m/z 367 (MH$^+$). Anal. Calcd. For $C_{20}H_{18}N_2O_5$: C, 65.57; H, 4.95; N, 7.65. Found: C, 65.97; H, 5.01; N, 7.3.

Preparation of compound 23. To a stirred solution of 22 (513 mg, 1.4 mmol) in THF 10 mL was cooled to −78° C., then LHMDS (1 Mol. THF sol. 1.7 mL, 1.68 mmol) was added slowly. The mixture was stirred for 30 min. at −78° C. and a pre-cooled (to −78° C.) stirred solution of $ICH_2CO_2^tBu$ in THF 3 mL was added to the above mixture at −78° C. Cooling bath was removed and the mixture was stirred for 2 hours at room temperature. The mixture was poured in to NH$_4$Cl aq. solution. Careful extraction by EA and the collected organic phase was dried by MgSO$_4$. Evaporation and purification by column chromatography gave 23 (377 mg, 56%) as slightly yellow oil. $^1$H NMR (CDCl$_3$) δ 8.18 (2 H, m), 7.48 (2 H, m), 7.33-7.24 (5 H, m), 6.04 (1 H, m), 5.24 (2 H, m), 5.00 (1 H, dd, J=3.5 and 8.4 Hz), 4.81 (1 H, m), 4.17-4.05 (2 H, m), 3.66 (1 H, t, J=9.4 Hz), 2.73 (1 H, dd, J=10.7 and 17.2 Hz), 2.52 (1 H, dd, J=3.7 and 17.2 Hz), 1.30 (9 H, s). FAB-MS (+VE) m/z 481 (MH$^+$). Anal. Calcd. For C$_{26}$H$_{28}$N$_2$O$_7$·0.2H$_2$O: C, 64.51; H, 5.91; N, 5.79. Found: C, 64.22; H, 5.82, N, 5.73.

Preparation of compound 24. To a stirred solution of 23 (240 mg, 0.5 mmol) in THF/H$_2$O=6 mL/2 mL was added H$_2$O$_2$ (30%, 306 mg, 3 mmol) at 0° C., then LiOH.H$_2$O (73 mg, 1.75 mmol) was added. The mixture was stirred for 6 hours at room temperature. Na$_2$SO$_3$ (378 mg, 3.0 mmol) was added to the above mixture at 0° C. followed by the careful addition of 1 N-HCl 6 mL. The mixture was extracted by EA/H$_2$O and the organic phase was collected, dried by MgSO$_4$ to be purified by column chromatography to give 24 (159 mg, 95%) as slightly yellow oil. $^1$H NMR (CDCl$_3$) 8.16 (2 H, m), 7.38 (2 H, m), 5.90 (1 H, m), 5.22-5.18 (2 H, m), 3.68 (1 H, t, J=9.2 Hz), 3.21 (1 H, m), 2.62 (1 H, dd, J=9.8 and 16.8 Hz), 2.49 (1 H, dd, J=4.3 and 16.8 Hz), 1.40 (9 H, s). FAB-MS (−VE) m/z 334 (M−H). Anal. Calcd. For C$_{17}$H$_{21}$NO$_6$·0.05H$_2$O: C, 60.72; H, 6.32; N, 4.17. Found: C, 60.37; H, 6.25; N, 4.18.

Preparation of compound 25. To a stirred mixture of 24 (463 mg, 1.30 mmol), 29' (468 mg, 1.00 mmol), HOBt (203 mg, 1.5 mmol) and EDCI.HCl (288 mg, 1.5 mmol) in anhydrous THF was added DIPEA (0.26 mL, 1.5 mmol) at 0° C. The mixture was stirred for 16 hours at room temperature then additional 24 (181 mg dissolved in anhydrous THF, 0.54 mmol), HOBt (45 mg, 0.33 mmol) EDCI.HCl (64 mg, 0.33 mmol) DIPEA (0.06 mL, 0.33 mmol) at 0° C. The whole mixture was stirred for 24 hours at room temperature. The mixture was poured into water and 1 N HCl 2 mL was added to the water and was carefully extracted by ethyl acetate. The EA layer was combined and was dried by MgSO$_4$ to be purified by column chromatography to give 25 (408 mg, 52%) as slightly yellow oil recovering starting material 24 (174 mg, 26%) and 23 (130 mg, 28%). $^1$H NMR (CDCl$_3$) 7.98 (2 H, m), 7.63 (1 H, d, J=7.7 Hz), 7.42 (1H, s), 7.33-7.25 (2 H, m), 7.17-7.11 (3 H, m), 7.01 (1.4 and 8.3 Hz), 6.65 (1 H, s), 6.43 (1 H, d, J=3.0 Hz), 6.09 (1 H, s), 5.85-5.64 (2 H, m), 5.48 (1 H, s), 5.14-5.07 (4 H, m), 4.46 (1 H, m), 4.10-3.99 (2 H, m), 3.46 (1 H, t, J=10.2 Hz), 3.24-3.16 (1 H, m), 3.13-3.01 (2 H, m), 2.88 (1 H, dd, J=6.3 and 15.1 Hz), 2.66-2.42 (3 H, m), 2.44 (3 H, s), 2.31 (1 H, m), 2.13-1.99 (2 H, m), 1.79 (10 H, m), 1.45 (9 H, s). FAB-MS (+VE) m/z 785 (MH$^+$).

Preparation of compound 26. To a stirred solution of 25 (50 mg, 0.0637 mmol) in anhydrous CH$_2$Cl$_2$ 18 mL was added 2$^{nd}$ Grubbs catalyst (27 mg, 0.0318 mmol) in anhydrous CH$_2$Cl$_2$ 7 mL under Argon. The mixture was refluxed at 65-68° C. for 24 hours. The mixture was cooled to room temperature to be evaporated by rotary evaporator. The remaining residue was purified by column chromatography to give 26 (48 mg, nearly 100%) as brown solid. $^1$H NMR (CDCl$_3$) 8.15-8.12 (3 H, m), 7.49 (1 H, t, J=5.9 Hz), 7.42 (2 H, d, J=8.8 Hz), 7.35 (1 H, s), 7.26-6.96 (3 H, m), 6.55 (1 H, s), 6.35 (1 H, d, J=3.1 Hz), 6.14 (1 H, s), 5.78 (1 H, m), 5.37 (1 H, m), 5.16 (1 H, s), 4.68 (1 H, m), 4.21 (1 H, dd, J=5.3 and 14.3 Hz), 4.11 (1 H, dd, J=2.3 and 9.6 Hz), 3.77 (1 H, dd, J=9.2 and 14.3 Hz), 3.65 (1 H, dd, J=6.1 and 13.3 Hz), 3.20 (1 H, dd, J=3.7 and 14.8 Hz), 3.11 (1 H, m), 2.86 (1 H, dd, J=11.9 and 17.4 Hz), 2.67 (1 H, m), 2.54-2.31 (2 H, m), 2.39 (3 H, s), 2.09 (3 H, m), 1.94-1.25 (10 H, m), 1.35 (9 H, s). FAB-MS (+VE) m/z 757 (MH$^+$).

Preparation of compound 27. General Procedure of Preparation of aluminum amalgam (Al—Hg). Aluminum (which was scratched by scissors, 8.5 mg, 0.315 mmol) was put to 10% KOH aq. solution until vigorous bubbles occurred. KOH was removed by decantation and Al was washed by water 3 mL 5 times. 2% aq. HgCl$_2$ solution was covered into Al for 3 minutes and was removed by decantation. Aluminum was washed by water 3 mL three times. 2% aq. HgCl$_2$ solution was covered into Aluminum again for 3 minutes. The HgCl$_2$ solution was removed by decantation and was washed by water 4 mL three times, EtOH 3 mL three times, and finally by ether 5 mL two times to give freshly prepared Al—Hg as gray solid.

To a stirred solution of 26 (48 mg, 0.063 mmol) in ether 3 mL/2 drops of water was added Al—Hg (8.5 mg (the weight of starting Al), 0.315 mmol). The mixture was refluxed at 65-70° C. for 30 minutes. The reaction was checked by TLC and additional freshly prepared Al—Hg (17 mg. 0.630 mmol) was added to the mixture. The mixture was refluxed for 1 hour and was cooled to room temperature. Careful evaporation of the mixture gave the intermediate amine. This completely dried intermediate was dissolved by CH$_2$Cl$_2$ 3 mL and i-Pr$_2$NEt (16.3 mg, 0.126 mmol) in CH$_2$Cl$_2$ 1 mL was added and then t-butyl oxaly chloride (16 mg, 0.095 mmol) in CH$_2$Cl$_2$ 1 mL was added to this solution at 0° C. The mixture was stirred for 3 hours at room temperature and was quenched by MeOH 4 drops. The mixture was evaporated and purified by column chromatography to give 27 (26 mg, 48% for two steps) as pale brown solid. $^1$H NMR (CDCl$_3$) 8.83 (1 H, s), 8.10 (1 H, d, J=8.6 Hz), 7.53-7.22 (7 H, m), 6.99-6.96 (2 H, m), 6.54 (1 H, s), 6.35 (1 H, d, J=3.1 Hz), 6.17 (1 H, s), 5.76 (1 H, m), 5.35 (1 H, m), 55.24 (1 H, s), 4.67 (1 H, m), 4.19 (1 H, dd, J=5.3 and 14.3 Hz), 3.98 (1 H, d, J=9.8 Hz), 3.77 (1 H, dd, J=9.2 and 14.3 Hz), 3.64 (1 H, dd, J=5.9 and 13.1 Hz), 3.17 (1 H, dd, J=3.9 and 14.8 Hz), 3.09 (1 H, m), 2.84 (1 H, dd, J=11.9 and 17.1 Hz), 2.67 (1 H, m), 2.46-2.01 (4 H, m), 2.39 (3 H, s), 1.90-1.18 (12 H, m), 1.60 (9 H, s), 1.34 (9 H, s). FAB-MS (+VE) m/z 855 (MH$^+$).

Preparation of compound 28. To a stirred mixture of 27 (94 mg, 0.11 mmol) and H$_2$O 0.6 mL was added the mixture of TFA/EDT=3.0 mL/0.3 mL at 0° C. The mixture was stirred for 1.5 hour at room temperature. The solvent was evaporated completely by high vacuum and the residue was solidified by hexane 0.5 mL/ether 1 mL mixture and the solid was collected to be dried. And the solid was dissolved by CH$_3$CN/H$_2$O=15 mL/10 mL mixture to be purified by preparative HPLC (linear gradient from 30% CH$_3$CN (0.1% TFA)/70% H$_2$O (0.1% TFA) to 100% CH$_3$CN (0.1% TFA)/0% H$_2$O over 30 min and it was eluted at 20.7 min. The solution was lyophilized to give 28 (25 mg, 31%) as pale pink solid. $^1$H NMR (DMSO-d$_6$) δ 10.64 (1 H, s), 8.49 (1 H, s), 8.23 (1 H, d, J=8.2 Hz), 7.66 (2 H, d, J=9.8 Hz), 7.54 (1 H, s), 7.38-7.27 (6 H, m), 7.09 (1 H, s), 6.94 (1 H, m), 6.31 (1 H, d, J=2.9 Hz), 5.73 (1 H, m), 5.49 (1 H, m), 4.30 (1 H, m), 4.19 (1 H, dd, J=6.1 and 14.1 Hz), 4.05 (1 H, d, J=11.3 Hz), 3.93 (1 H, 8.4 and 14.3 Hz), 3.46 (1 H, dd, J=6.1 and 12.9 Hz), 3.28 (1 H, d, J=11.7 Hz), 2.85 (1 H, dd, J=5.1 and 15.4 Hz), 2.73 (1 H, dd, J=12.1 and 16.6 Hz), 2.52 (1 H, m (hidden from DMSO solvent peak)), 2.36 (3 H, s), 2.36-2.24 (2 H, m), 1.99-1.73 (7 H, m), 1.49 (5 H, m), 1.19 (1 H, m). FAB-MS (−VE) m/z 741 (M−H).

Compounds 32-33 of the invention are prepared as shown in FIG. 3.

Preparation of compound 30. To a stirred mixture of 29' (281 mg, 0.6 mmol), compound 29 (363 mg, 0.72 mmol), 1-hydroxy-7-azabenzotriazole (HOAt) (0.5 Mol. 1.8 mL, 0.9 mmol) in DMF 8 mL was added EDCI.HCl (173 mg, 0.9 mmol). The mixture was stirred for 1 hr. at room temperature then 22 hours at 70-75° C. DMF was removed by high vacuum and the residue was purified by column chromatography to give 30 (110 mg, 19%) as yellow oil. $^1$H NMR (CDCl$_3$) 7.49 (1 H, t, J=5.5 Hz), 7.40-7.17 (9 H, m), 7.01 (1 H, d, J=8.6 Hz), 6.39 (1 H, d, J=3.1 Hz), 6.09 (1H, s), 5.99 (1 H, s), 5.77 (2 H, m), 5.32 (1 H, s), 5.15-5.02 (4 H, m), 4.44 (1 H, m), 4.38 (1 H, s), 4.15 (1 H, dd, J=6.6 and 14.6 Hz), 4.00 (1 H, dd, J=7.6 and 14.4 Hz), 3.40 (1 H, t, J=10.4 Hz), 3.24 (2 H, m), 2.98 (1 H, m), 2.78 (2 H, m), 2.63-2.57 (2 H, m), 2.44 (3 H, s), 2.36 (1 H, m), 2.06 (2 H, m), 1.66 (4 H, m), 1.46 (18 H, s), 1.42 (9 H, s), 1.30-1.23 (2 H, m), 1.10-1.04 (3 H, m), 0.43 (1 H, m). FAB-MS (+VE) m/z 954 (MH$^+$).

Preparation of compound 31. To a stirred solution of 30 (95.4 mg, 0.1 mmol) in anhydrous CH$_2$Cl$_2$ 95 mL was added 2$^{nd}$ Grubbs catalyst (42 mg, 0.05 mmol). The mixture was refluxed at 66° C. for 23 hours under Argon. The mixture was cooled to room temperature to be evaporated by rotary evaporator. The remaining residue was purified by column chromatography to give 31 (75 mg, 81%) as yellow oil. $^1$H NMR (CDCl$_3$) 8.11 (1 H, d, J=8.6 Hz), 7.51 (1H, t, J=5.3 Hz), 7.36-7.19 (7 H, m), 7.03-6.97 (2 H, m), 6.36 (2 H, m), 5.96 (1 H, s), 5.76 (1 H, dd, J=9.0 and 14.6 Hz), 5.35 (1 H, m), 5.16 (1 H, s), 4.68 (1 H, m), 4.38 (1 H, s), 4.21 (1 H, dd, J=5.3 and 14.3 Hz), 3.98 (1 H, d, J=10.0 Hz), 3.79 (1 H, dd, J=9.4 and 14.3 Hz), 3.65 (1 H, dd, J=5.7 and 13.5 Hz), 3.17 (1 H, dd, J=3.5 and 14.7 Hz), 3.06 (1 H, d, J=12.0 Hz), 2.85 (1 H, m), 2.66 (1 H, m), 2.44 (1 H, m), 2.39 (3 H, s), 2.32 (1 H, dd, J=5.9 and 15 Hz), 2.23 (1 H, m), 2.07 (2 H, m), 1.90-1.26 (10 H, m), 1.45 (18 H, s), 1.35 (9 H, s). FAB-MS (+VE) m/z 926 (MH$^+$).

Preparation of compound 32. A mixture of TFA/H$_2$O/EDT=3 mL/0.1 mL/0.1 mL was added to 31 (74 mg, 0.08 mmol) at rt. The mixture was stirred for 1.5 hour at room temperature. The solvent was evaporated completely by high vacuum and the residue was solidified by diethyl ether 2 mL and the solid was dissolved by CH$_3$CN/H$_2$O/TFA 7 mL/1 mL/0.1 mL and was purified by preparative HPLC (linear gradient: 80% H$_2$O (0.1% TFA)/20% CH$_3$CN (0.1% TFA) for 4 minutes and then from 80% CH$_3$CN/20% H$_2$O to 50% CH$_3$CN/50% H$_2$O over 16 min followed by 100% CH$_3$CN/0% H$_2$O over 10 min. and it was eluted at 24.5 min. The solution was lyophilized to give 32 (23 mg, 38%) as white solid. $^1$H NMR (DMSO-d$_6$) δ 8.54 (1 H, s), 8.31 (1 H, d, J=8.2 Hz), 7.56 (1 H, s), 7.38-7.24 (8 H, m), 7.11 (1 H, s), 6.95 (1 H, m), 6.31 (1 H, d, J=3.1 Hz), 5.75 (1 H, dd, J=10.3 and 15.2 Hz), 5.49 (1 H, m), 4.59 (1 H, s), 4.27 (1 H, m), 4.19 (1 H, dd, J=6.4 and 14.5 Hz), 4.11 (1 H, d, J=10.2 Hz), 3.94 (1 H, dd, J=7.8 and 14.1 Hz), 3.47 (1 H, m), 3.30 (1 H, d, J=12.3 Hz), 2.85 (1 H, dd, J=4.9 and 15.4 Hz), 2.76 (1 H, dd, J=12.1 and 16.6 Hz), 2.50 (1 H, m), 2.36 (3 H, s), 2.36-2.31 (2 H, m), 1.97 (4 H, m), 1.80 (3 H, m), 1.49 (5 H, m), 1.18 (1 H, m). FAB-MS (−VE) m/z 756 (M−H).

Preparation of compound 33. To a stirred suspension of 32 (20 mg, 0.0264 mmol) in H$_2$O 3 mL was added LiOH.H$_2$O (11 mg, 0.2640 mmol) and the whole mixture was stirred for 4 hours at room temperature. The mixture was neutralized by TFA (30 mg, 0.2640 mmol) in H$_2$O 0.2 mL at 0° C. and was directly purified by HPLC (linear gradient: 80% H$_2$O (0.1% TFA)/20% CH$_3$CN (0.1% TFA) for 4 minutes and then from 80% CH$_3$CN/20% H$_2$O to 50% CH$_3$CN/50% H$_2$O over 16 min followed by 100% CH$_3$CN/0% H$_2$O over 10 min. and it was eluted at 25.8 min. The solution was lyophilized to give 33 (3.5 mg, 19%) as white solid recovering 32 (9 mg, 45%). $^1$H NMR (DMSO-d$_6$) δ 8.53 (1 H, s), 8.27 (1 H, d, J=8.0 Hz), 7.55 (1 H, s), 7.38-7.16 (8 H, m), 7.09 (1 H, s), 6.95 (1 H, m), 6.31 (1 H, d, J=2.7 Hz), 5.74 (1 H, dd, J=9.8 and 14.8 Hz), 5.48 (1 H, m), 4.28 (1 H, m), 4.19 (1 H, dd, J=6.4 and 14.2 Hz), 4.08 (1 H, d, J=11.3 Hz), 3.93 (1 H, dd, J=8.8 and 14.1 Hz), 3.47 (3 H, m, hidden from water peak), 3.29 (1 H, m), 2.84 (1 H, dd, J=5.1 and 15.8 Hz), 2.74 (1 H, dd, J=12.1 and 16.4 Hz), 2.50 (1 H, m), 2.36 (3 H, s), 2.36-2.31 (2 H, m), 1.97 (4 H, m), 1.80 (3 H, m), 1.49 (5 H, m), 1.20 (1 H, m). FAB-MS (−VE) m/z 712 (M−H).

Compound 41 is prepared as shown in FIG. 4.

Preparation of compound 34. To a stirred solution of commercially available hypophosphorous acid (50% wt. aq. solution. 100 g, 757.6 mmol) was carefully added ammonium hydroxide (28-30%, 92 g, 760 mmol) at 0° C. and the mixture was stirred for 1 hour at room temperature. The mixture was directly freeze-dried to give wet white solid. This solid was dried over P$_2$O$_5$ under high vacuum. This freshly prepared small portion ammonium phosphinate (6 g, 72 mmol) and hexamethyl disilazane (15.2 mL, 72 mmol) mixture was heated with stirring to 110° C. for 1.6 hr. under Argon. The system (exercising care, as fume is highly flammable in air) was cooled to 0° C., and dichloromethane 70 mL was injected followed by the benzyl bromide (7.14 mL, 60 mmol). The mixture was stirred for 1 hr. at RT and then 1.5 hr at 65° C. The mixture was cooled to 0° C. then hexamethyldisilazane (15.2 mL, 72 mmol) was added. The system was refluxed for 1 hour, cooled to 0° C., 4-bromobenzyl bromide was added, refluxed for 2 hours. The solid was filtered off and the residue was evaporated to be purified by column chromatography to give intermediate di-alkylintermediate phosphinic acid as yellow solid (5.6 g, 29%) showing the product is the mixture of di-benzylated and mono-benzylated mixture by NMR and FAB Mass. This intermediate (5 g, 15.4 mmol) was dissolved by anhydrous CH$_2$Cl$_2$ 60 mL and t-Butyl-2,2,2-trichloroacetimidate (3 mL, 16.9 mmol) in anhydrous cyclohexane 60 mL was slowly added to the mixture then BF$_3$.Et$_2$ 0.2 mL was added. The mixture was stirred overnight at room temperature and the solid was filtered-off. The residue was evaporated and purified by column chromatography to give 34 (4.6 g, 78%, mixture of inseparable di-benzylated compound) as white solid. $^1$H NMR (CDCl$_3$) δ 7.41 (2 H, d, J=8.4 Hz), 7.32-7.21 (5 H, m), 7.11 (2 H, dd, J=2.3 and 8.6 Hz), 3.04 (2 H, d, J=16.4 Hz), 2.95 (2 H, d, J=15.8 Hz), 1.29 (9 H, s). FAB-MS (+VE) m/z 381 (MH$^+$).

Preparation of compound 35. The stirred mixture of 34 (60%, 4.1 g, 6.5 mmol), Oxazolidinone derivative (34', 1.4 g, 6.5 mmol), tri-o-tolyl-phosphine (989 mg, 3.25 mmol), Pd(OAc)$_2$ (292 mg, 1.3 mmol) in Et$_3$N 60 mL was refluxed at 120° C. for 1.5 hour. The mixture was cooled to room temperature to be extracted by NH$_4$Cl aq. solution/CHCl$_3$. The CHCl$_3$ layer was collected and dried by MgSO$_4$. The evaporation followed by purification through column chromatography to give 35 (3.1 g, 92% yield) as pale yellow solid. Mp 158-160° C. $^1$H NMR (CDCl$_3$) 7.91 (1 H, dd, J=0.6 and 15.6 Hz), 7.76 (1 H, d, J=15.8 Hz), 7.52 (2 H, d, J=8.2 Hz), 7.42-7.23 (12 H, m), 5.56 (1H, dd, J=3.9 and 8.6 Hz), 4.74 (1 H, t, J=8.8 Hz), 4.32 (1 H, dd, J=3.9 and 8.8 Hz), 3.04 (2 H, d, J=16.2 Hz), 3.03 (2 H, d, J=16.2 Hz), 1.28 (9 H, s). FAB-MS (+VE) m/z 518 (MH$^+$).

Preparation of compound 36. To a stirred slurry of PhSCu (1.2 g, 6.96 mmol) in dry ether 150 mL under Ar at −45° C. was added vinylmagnesium bromide (17.4 mL of 1 Mol solution in THF, 17.4 mmol) dropwise. The mixture was stirred for 20 min. at −20° C. and was cooled again to −45° C. and pre-cooled (to 0° C.) solution of 35 (3 g, 5.80 mmol) in anhydrous THF/CH$_2$Cl$_2$=30 mL/20 mL was added dropwise via cannula at −45° C. The mixture was stirred for 0.5 hr. at −40° C. and was poured into NH$_4$Cl aqueous solution. Careful extraction with EA and purification by column chromatography gave 36 (1.4 g, 44%) as white solid. Mp 155-157° C. $^1$H NMR (CDCl$_3$) 7.37-7.20 (10 H, m), 7.15 (4 H, s), 5.95 (1 H, m), 5.31 (1 H, m), 4.99-4.91 (2 H, m), 4.58 (1 H, t, J=8.8 Hz), 4.24-4.20 (1 H, m), 3.88 (1 H, m), 3.49-3.32 (2 H, m), 3.01 (2 H, d, J=16.0 Hz), 2.98 (2 H, d, J=16.2 Hz), 1.28 (9H, s). FAB-MS (+VE) m/z 546 (MH$^+$).

Preparation of compound 37. To a stirred solution of 36 (1 g, 1.83 mmol) in anhydrous THF 30 mL under Argon was added NaHMDS (2.2 mL 2.2 mmol) dropwise at −78° C. and the mixture was stirred for 5 min. at −78° C. ICH$_2$CO$_2$$^t$Bu (576 mg, 2.38 mmol) in THF 3 mL was added to the above mixture at −78° C. dropwise and the mixture was stirred for 5 min. at −78° C. Dry ice/acetone bath was removed and the mixture as stirred for 40 minutes at room temperature. The mixture was extracted by NH$_4$Cl aq. solution/EA. The organic phase was collected to be dried by MgSO$_4$ and was evaporated to be purified by column chromatography to give 37 (480 mg, 40%) as yellow oil recovering the starting material (200 mg, 20%). $^1$H NMR (CDCl$_3$) 7.31-7.15 (14 H, m), 6.08 (1 H, m), 5.19-5.15 (2 H, m), 4.93 (1 H, dd, J=2.8 and 8.6 Hz). 4.77 (1 H, m), 4.20 (1 H, t, J=8.6 Hz), 3.98 (1 H, dd, J=2.8 and 8.8 Hz), 3.38 (1 H, t, J=9.7 Hz), 3.03 (4 H, m), 2.75 (1 H, dd, J=11.1 and 17.2 Hz), 2.59 (1 H, dd, J=3.7 and 17.2 Hz), 1.34 (9 H, s), 1.29 (9 H, s). FAB-MS (+VE) m/z 660 (MH$^+$).

Preparation of compound 38. To a stirred solution of 37 (500 mg, 0.758 mmol) in THF/H$_2$O=8 mL/2 mL was added H$_2$O$_2$ (30%, 0.62 mL, 6.064 mmol) at 0° C., then LiOH.H$_2$O (127 mg, 3.031 mmol) was added. The mixture was stirred for 4 hours at room temperature. Na$_2$SO$_3$ (764 mg, 6.064 mmol) was added to the above mixture at 0° C. followed by the careful addition of 1 N-HCl 6.1 mL. The mixture was extracted by EA/H$_2$O and the organic phase was collected, dried by MgSO$_4$ to be purified by column chromatography to give 38 (330 mg, 85%) as white solid. Mp 150-152° C. $^1$H NMR (CDCl$_3$) 7.26-7.17 (5 H, m), 7.09 (2 H, m), 7.02 (2 H, m), 5.94 (1 H, m), 5.18-5.09 (2 H, m), 3.49 (1 H, t, J=9.8 Hz), 3.21-3.13 (1 H, m), 3.50-2.56 (6 H, m), 1.44 (9 H, s), 1.16 (9 H, s). FAB-MS (−VE) m/z 513 (M−H).

Preparation of compound 39. To a stirred mixture of 38 (576 mg, 1.12 mmol) in DMF 5 mL was added HOAt (2.24 mL of 0.5 Mol in DMF, 1.12 mmol) followed by EDCI.HCl (215 mg, 1.12 mmol) at room temperature. The mixture was stirred for 10 minutes and then 29' (374 mg, 0.8 mmol) along with additional DMF 3 mL was added to this mixture. The mixture was stirred for 1 hour at room temperature then 30 hours at 40~45° C. DMF was removed by high vacuum remaining 1 mL residue. This residue was purified by column chromatography to give 39 (320 mg, 42% yield) as yellow oil recovering starting material 137B-35 (130 mg, 35%). $^1$H NMR (CDCl$_3$) 7.39-7.00 (16 H, m), 6.50 (1 H, s), 6.40 (1H, d, J=3.1 Hz), 5.76 (1 H, m), 5.51 (1 H, d, J=7.6 Hz), 5.12-5.00 (4 H, m), 4.46 (1 H, m), 4.11 (1 H, m), 4.00 (1 H, dd, J=7.2 14.7 Hz), 3.37 (1 H, t, J=10.2 Hz), 3.21 (1 H, m), 3.16-2.88 (6 H, m), 2.76 (2 H, m), 2.59 (2 H, m), 2.44 (3 H, s), 2.31 (1 H, m) 2.04 (2 H, m), 1.92 (1 H, s), 1.80-1.50 (4 H, m), 1.43 (9 H, s), 1.28 (9 H, d, J=18.0 Hz), 1.43-1.10 (4 H, m), 0.67 (1 H, s). FAB-MS (+VE) m/z 964 (MH$^+$).

Preparation of compound 40. To a stirred mixture of 39 (212 mg, 0.22 mmol) and 2$^{nd}$ Grubbs catalyst (93 mg, 0.11 mmol I) in anhydrous CH$_2$Cl$_2$ 200 mL was refluxed at 65° C. for 20 hours. The mixture was cooled to room temperature to be evaporated by rotary evaporator. The remaining residue was purified by column chromatography to give 40 (182 mg, 88%) as yellow oil. $^1$H NMR (CDCl$_3$) 8.15 (1 H, d, J=8.6 Hz), 7.54 (1 H, t, J=5.5 Hz), 7.33-7.09 (11 H, m), 6.95 (2 H, m), 6.73 (1 H, s), 6.55 (1 H, s), 6.32 (1 H, d, J=3.1 Hz), 5.76 (1 H, dd, J=10.3 and 14.1 Hz), 5.40 (1 H, s), 5.29 (1 H, s), 4.65 (1 H, s), 4.15 (1 H, dd, J=5.7 and 14.3 Hz), 3.99 (1 H, d, J=8.0 Hz), 3.77 (1 H, dd, J=9.0 and 14.3 Hz), 3.63 (1 H, dd, J=5.9 and 13.3 Hz), 3.15 (2 H, m), 3.01-2.80 (5 H, m), 2.66 (1 H, m), 2.36 (3 H, s), 2.49-2.27 (2 H, m), 2.17-2.00 (3 H, m), 1.94-1.63 (7 H, m), 1.31 (9 H, s), 1.22 (9 H, d, J=5.9 Hz), 1.55-1.14 (3 H, m). FAB-MS (+VE) m/z 936 (MH$^+$).

Preparation of compound 41. The mixture of TFA/H$_2$O/EDT=3 mL/0.1 mL/0.1 mL was added to 40 (94 mg, 0.10 mmol) at 0° C. The mixture was stirred for 1.2 hour at room temperature. The solvent was evaporated completely by high vacuum and the residue was dissolved by CH$_3$CN/H$_2$O=1.5 mL/1.5 mL and was purified by preparative HPLC (linear gradient: 90% H$_2$O/10% CH$_3$CN for 4 minutes and then from 30% CH$_3$CN (0.1% TFA)/70% H$_2$O (0.1% TFA) to 100% CH$_3$CN (0.1% TFA)/0% H$_2$O over 30 min and it was eluted at 19.8 min. The solution was lyophilized to give 41 (30 mg, 36%) as pale pink solid. $^1$H NMR (DMSO-d$_6$) δ 8.52 (1 H, s), 8.27 (1 H, d, J=8.2 Hz), 7.55 (1 H, s), 7.38-7.10 (14 H, m), 6.95 (1 H, m), 6.31 (1 H, d, J=2.3 Hz), 5.74 (1 H, dd, J=10.1 and 14.4 Hz), 5.48 (1 H, m), 4.28 (1 H, m), 4.19 (1 H, dd, J=7.0 and 14.4 Hz), 4.07 (1 H, d, J=9.8 Hz), 3.93 (1 H, dd, J=8.0 and 14.4 Hz), 3.46 (1 H, dd, J=7.1 and 13.1 Hz), 3.28 (1 H, d, J=12.1 Hz), 2.97 (4 H, t, J=16.2 Hz), 2.85 (1 H, dd, J=4.7 and 15.6 Hz), 2.74 (1 H, dd, J=12.5 and 17.0 Hz), 2.50 (1 H, m), 2.36 (3 H, s), 2.36-2.31 (2 H, m), 2.00-1.73 (8 H, m), 1.56-1.42 (5 H, m), 1.19 (1 H, m). FAB-MS (−VE) m/z 822 (M−H).

Compounds 46 and 49 are prepared as shown in FIG. 5.

Preparation of compound 42. Ammonium phosphinate, 6 g (72 mmol, 1.2 eq.) and hexamethyldisilazane (15.2 mL, 72 mmol, 1.2 eq.) were heated together to 110° C. for 1.5 hour under Argon with stirring. The mixture was cooled to 0° C. and DCM 70 mL was injected followed by 4-bromobenzyl bromide (15 g, 60 mmol, 1 eq.). The whole mixture was stirred overnight at 30° C. Additional hexamethyldisilazane (15.2 mL, 72 mmol, 1.2 eq.) was added. The mixture was stirred for 2 hours at 30° C., then MeI (5.6 mL, 90 mmol, 1.5 eq.) was added. The mixture was stirred overnight at 30° C. The mixture was poured into cold water 100 mL carefully, then extracted by chloroform 200 mL three times. The combined chloroform was dried by MgSO$_4$, evaporated and dried by high vacuum. The residue was dissolved by anhydrous DCM 30 mL and t-Butyl-2,2,2-trichloroacetimidate. (13 mL, 72 mmol, 1.2 eq.) in anhydrous cyclohexane 60 mL was added slowly, followed by BF$_3$.OEt$_2$ (0.1 mL, catalytic amount) dropwise at room temperature. The whole mixture was stirred for 2 hours at rt and was quenched by solid NaHCO$_3$ 200 mg. The solid was filtered and the solid was washed by DCM two times and the solid was discarded. The combined residue was purified by careful chromatography to give 42 as white solid (6.1 g, 33% for three steps). $^1$H NMR (CDCl$_3$) 7.43 (2 H, d, J=7.8 Hz), 7.15 (2 H, dd, J=2.5 and 8.6 Hz), 3.04 (2 H, 17.4 Hz), 1.45 (9 H, s), 1.37 (3 H, d, J=13.7 Hz). FAB-MS (+VE) m/z 305 (MH$^+$).

Preparation of compound 43. The stirred mixture of 42 (4.3 g, 14 mmol), Oxazolidinone derivative (42', 3.0 g, 14 mmol), tri-o-tolyl-phosphine (2.13 g, 7.0 mmol), Pd(OAc)$_2$ (629 mg, 2.8 mmol) in Et$_3$N 70 mL was refluxed at 115° C. for 1.5 hour. The mixture was poured into cold water and was extracted by DCM. The collected DCM was dried by MgSO$_4$, the evaporation by rotary evaporator and followed by purification through column chromatography to give 43 (4.5 g, 73% yield) as pale yellow solid. $^1$H NMR (CDCl$_3$) 7.91 (1 H, dd, J=0.8 and 15.8 Hz), 7.76 (1 H, d, J=15.6 Hz), 7.53 (2 H, d, J=8.0 Hz), 7.44-7.27 (7 H, m), 5.56 (1H, dd, J=3.9 and 8.6 Hz), 4.74

(1 H, t, J=9.0 Hz), 4.32 (1 H, dd, J=3.9 and 8.8 Hz), 3.11 (2 H, d, J=17.8 Hz), 1.45 (9 H, s), 1.37 (3 H, d, J=13.7 Hz), FAB-MS (+VE) m/z 442 (MH⁺).

Preparation of compound 44. This compound was prepared by a procedure similar to that of preparing compound 36, and obtained 3.5 g (76%) as yellow solid. ¹H NMR (CDCl₃) 7.38-7.12 (9 H, m), 5.95 (1 H, m), 5.32 (1 H, m), 5.01-4.92 (2 H, m), 4.60 (1 H, m), 4.23 (1 H, m), 3.88 (1 H, m), 3.50-3.31 (2 H, m), 3.04 (2 H, m), 1.47 (9 H, s), 1.34 (3 H, d, J=13.7 Hz), FAB-MS (+VE) m/z 470 (MH⁺).

Preparation of compound 45. To a stirred solution of 44 (3.8 g, 1.83 mmol) in anhydrous THF 60 mL under Argon was added NaHMDS (2.2 mL 2.2 mmol, pre-cooled to −78° C.) in THF 30 mL slowly at −78° C. via cannula and the mixture was stirred for 2 min. at −78° C. ICH₂CO₂ᵗBu (2.35 g, 9.713 mmol) in THF 10 mL was added slowly to the above mixture at −78° C. The dry ice/acetone bath was removed and the stirring was continued for 30 minutes and was poured into NH₄Cl aq. solution. The extractive work-up with EA and purification by column chromatography gave 45-1 (upper spot on TLC plate) and 45-2 (lower spot on TLC plate) as two diastereomers about 1:1 mixture (2.9 g, 61%, combined yield) as yellow oil. ¹H NMR (45-1, CDCl₃) 7.28-7.22 (9 H, m), 6.08 (1 H, m), 5.20-5.16 (2 H, m), 4.92 (1 H, dd, J=2.4 and 8.4 Hz), 4.78 (1 H, m), 4.17 (1 H, t, J=8.6 Hz), 3.95 (1 H, dd, J=2.7 and 8.8 Hz), 3.35 (1 H, t, J=10.0 Hz), 3.15-2.98 (2 H, m), 2.75 (1 H, dd, J=11.5 and 17.6 Hz), 2.61 (1 H, dd, J=3.7 and 17.2 Hz), 1.51 (9 H, s), 1.41 (3 H, d, J=13.7 Hz), 1.30 (9 H, s). ¹H NMR (45-2, CDCl₃) 7.34-7.15 (9 H, m), 6.07 (1 H, m), 5.19-5.15 (2 H, m), 4.87 (1 H, m). 4.78 (1 H, m), 4.05 (1 H, t, J=8.4 Hz), 3.96 (1 H, m), 3.38 (1 H, t, J=9.4 Hz), 3.3.15-3.00 (2 H, m), 2.74 (1 H, dd, J=11.2 and 17.2 Hz), 2.57 (1 H, dd, J=3.9 and 17.4 Hz), 1.51 (9 H, s), 1.38 (3 H, d, J=13.7 Hz), 1.30 (9 H, s).

Preparation of compound 46. 45-1 (12 mg, 0.02 mmol) was dissolved from the TLC plate by DCM 0.8 mL and was treated with TFA at 0° C. The mixture was stirred for 1.5 hour at room temperature and the solvent was removed completely by high vacuum. 45-2 was subjected to the same procedure and each dried sample was dissolved in DMSO-d₆ for NMR interpretation, which showed identical NMR peaks. ¹H NMR (DMSO-d₆) 7.32-7.15 (9 H, m), 6.15 (1 H, m), 5.24-5.13 (2 H, m), 4.99 (1 H, d, J=7.6), 4.62 (1 H, m), 4.11 (1 H, t, J=8.6 Hz), 3.89 (1 H, d, J=8.8 Hz), 3.44 (1 H, t, J=9.2 Hz), 3.04 (2 H, d, J=17.8 Hz), 2.68 (1 H, dd, J=11.5 and 17.4 Hz), 2.51-2.44 (1 H, m), 1.26 (3 H, d, J=14.1 Hz). This test confirmed the presence of diastereoisomers and that pure diastereomers can be isolated.

Preparation of compound 47. The intermediate acid was prepared according to the procedure of preparing 38, from 45-1 (642 mg, 1.1 mmol). The intermediate was roughly purified by short flash column chromatography keeping the column cool, by pouring previously cooled (∼−10° C.) solvent system increasing the gradient slowly (from Chloroform: MeOH=20:1 to 10:1). This intermediate acid was activated by HOAt (0.5 Mol. in DMF, 1.6 mL, 0.88 mmol), DIPCDI (153 mg, 1.1 mmol) in DMF 5 mL for 10 min., and then 29' (360 mg, 0.77 mmol) in DMF 2 mL was added to this mixture. The mixture was stirred for 30 minutes at room temperature and then 20 hours at 40° C. DMF was removed by high vacuum distillation remaining 1 mL residue. This residue was purified by column chromatography to give 47 (240 mg, 31% yield for 2 steps) as yellow oil recovering starting material 29' (120 mg, 37%). ¹H NMR (CDCl₃) 7.39-7.00 (11 H, m), 6.39 (1 H, d, J=3.1 Hz), 6.24 (1 H, s), 5.83-5.67 (2 H, m), 5.41 (1 H, s), 5.12-5.02 (4 H, m), 4.46 (1 H, m), 4.10 (1 H, dd, J=7.2 and 14.6 Hz), 4.01 (1 H, dd, J=7.4 and 14.8 Hz), 3.37 (1 H, t, J=10.3 Hz), 3.21 (1 H, m), 3.12 (1 H, m), 3.05-2.88 (3 H, m), 2.76 (2 H, m), 2.58 (2 H, m), 2.44 (3 H, s), 2.31 (1 H, m) 2.04 (2 H, m), 1.72 (5 H, m), 1.48 (9 H, s), 1.43 (9 H, s), 1.32 (3 H, d, J=13.7 Hz), 0.70 (1 H, s).

Preparation of compound 48. This compound was prepared by a procedure substantially same as that for preparing compound 40. The yield was quantitative (contaminated with Grubbs Catalyst). ¹H NMR (CDCl₃) 8.12 (1 H, d, J=8.6 Hz), 7.54 (1 H, t, J=5.4 Hz), 7.35-6.95 (8 H, m), 6.68 (1 H, s), 6.39 (1 H, s), 6.34 (1 H, d, J=2.9 Hz), 5.75 (1 H, dd, J=10.3 and 15.8 Hz), 5.37 (1 H, m), 5.30 (1 H, s), 4.66 (1 H, m), 4.18 (1 H, dd, J=5.5 and 14.5 Hz), 3.98 (1 H, d, J=9.9 Hz), 3.77 (1 H, dd, J=9.4 and 14.3 Hz), 3.64 (1 H, dd, J=5.7 and 12.9 Hz), 3.14 (2 H, m), 3.06-2.79 (5 H, m), 2.66 (1H, m), 2.36 (3 H, s), 2.46-2.28 (2 H, m), 2.20-2.00 (3 H, m), 1.90-1.62 (7 H, m), 1.41 (9 H, s), 1.33 (9 H, s), 1.59-1.19 (6 H, m).

Preparation of compound 49. This compound was prepared by a procedure substantially same as the procedure to prepare compound 41. Linear gradient: 90% H₂O/10% CH₃CN for 4 minutes and then from 25% CH₃CN (0.1% TFA)/75% H₂O (0.1% TFA) to 100% CH₃CN (0.1% TFA)/0% H₂O over 30 min and it was eluted at 18.1 min. The solution was lyophilized to give 49 (56 mg, 46%) as pale pink solid. ¹H NMR (DMSO-d₆) δ 8.52 (1 H, s), 8.27 (1 H, d, J=7.8 Hz), 7.55 (1 H, s), 7.38-7.10 (9 H, m), 6.95 (1 H, d, J=8.2 Hz), 6.31 (1 H, d, J=2.7 Hz), 5.74 (1 H, m), 5.48 (1 H, m), 4.29 (1 H, m), 4.19 (1 H, dd, J=6.2 and 15.0 Hz), 4.07 (1 H, d, J=10.0 Hz), 3.93 (1 H, dd, J=8.4 and 14.1 Hz), 3.47 (1 H, m), 3.28 (1 H, d, J=11.5 Hz), 2.98 (2 H, d, J=16.8 Hz), 2.87 (1 H, dd, J=4.1 and 15.0 Hz), 2.74 (1 H, dd, J=12.2 and 16.2 Hz), 2.36 (3 H, s), 2.50-2.31 (3 H, m), 2.00-1.74 (8 H, m), 1.51-1.45 (5 H, m), 1.18 (3 H, d, J=13.9 Hz), 1.20-1.17 (1 H, m).

Compound 61, which is a mixture of diastereoisomers, can be prepared as shown in FIG. 6A-6B.

2-[(5-methyl-1H-indol-1-yl)methyl]pent-4-enenitrile (51). To a stirred solution of LDA 2.0 M in THF (57.5 mL, 115 mmol) was added dropwise a solution of 50 (17.67 g, 95.9 mmol) in THF (300 mL) at −78° C. under argon. The solution was stirred at −78° C. (2 h), then allyl bromide (15.2 g, 125 mmol) in THF (70 mL) was added and the mixture was stirred for an additional 2 h at −78° C. The reaction mixture was warmed to room temperature and stirred overnight. The reaction was quenched by the addition of ice-cold saturated NH₄Cl solution (200 mL), extracted with EtOAc, washed with brine and dried (Na₂SO₄). Evaporation provided a residue, which was purified by silica gel flash chromatography to provide 51 as colorless oil. (8.91 g, 41% yield). H NMR (d⁶-DMSO) δ 7.47 (d, 1H, J=8.5 Hz), 7.35 (d, 1H, J=3.1 Hz), 7.32 (s, 1H), 6.97 (d, 1H, J=8.4 Hz), 6.38 (d, 1H, J=3.2 Hz), 5.84 (m, 1H), 5.21-5.15 (m, 2H), 4.47 (dd, 1H, J=8.3 Hz & 14.4 Hz), 4.40 (dd, 1H, J=6.2 Hz & 14.4 Hz), 3.45 (m, 1H), 2.37 (s, 3H), 2.35-2.25 (m, 2 H). FABMS (+Ve) m/z 224 [M+], 225 [MH⁺].

2-[(5-methylindolyl)methyl]pent-4-enylamine (52). To a stirred solution of 51 (8.82 g, 39.3 mmol) in THF (400 mL) at 0° C. was added LiAlH₄ (4.77 g, 118 mmol). The mixture was stirred at room temperature overnight, then cooled to −78° C. and ethyl acetate (60 mL) was added followed by 10% NaOH_aq (15 mL). The reaction was quenched by the addition of moister Na₂SO₄, filtered through celite, washed with EtOAc (3×100 mL) and MeOH (3×150 mL). Evaporation provided a residue, which was purified by silica gel flash chromatography to provide 52 as colorless oil. (3.52 g, 39% yield). H NMR (d⁶-DMSO) δ 7.34-7.27 (m, 3H), 6.93 (d, 1H, J=1.5 Hz & 8.3 Hz), 6.31 (d, 1H, J=3.0 Hz), 5.78 (m, 1H), 5.06-4.99 (m, 2H), 4.16 (dd, 1H, J=7.0 Hz & 14.2 Hz), 4.00 (dd, 1H, J=6.5 Hz & 14.2 Hz), 2.42 (t, 2H, J=4.5 Hz), 2.36 (s, 3H), 2.05 (m, 1 H), 1.98-1.90 (m, 2H). FABMS (+Ve) m/z 229 [MH$^+$].

N-2-[(5-methylindolyl)methyl]pent-4-enyl(2S)-3-carbamoyl-2-({[[(fluoren-9-ylmethoxy)carbonylamino]cyclohexyl}carbonylamino) propanamide (55). To a solution of 52 (3.19 g, 14.0 mmol) in DMF (69 mL) was added a preactivated acid (prepared by the reaction of Boc-Asn-OH (3.41 g, 14.7 mmol), HOBt (1.98 g, 14.7 mmol) and DIPCDI (2.31 mL, 14.7 mmol) in DMF (46 mL) at room temperature for 10 min). The resulting solution was stirred at room temperature for 10 h. After solvent was evaporated, the residue was dissolved in EtOAc, washed with water, brine, dried over $Na_2SO_4$. Evaporation provided product 53 (6.5 g). To the solution of 53 (5.97 g, 13.5 mmol) in $CH_3CN$ (160 mL) was added 2 N $HCl_{aq}$ (160 mL). The resulting solution was stirred at room temperature for 15 h. After neutralization with saturated $NaHCO_{3aq}$ and evaporation of organic solvent, the mixture was extracted with EtOAc, washed with water, brine, dried over $Na_2SO_4$. The solvent was removed and the residue was purified by silica gel flash chromatography to provide 54 as colorless oil (3.40 g). To a solution of 54 (3.38 g, 9.88 mmol) and Fmoc-1-amino-cyclohexenecarboxylic acid (3.98 g, 9.88 mmol) in DMF (60 mL) was added HOBt (1.47 g, 9.88 mmol) and EDCI.HCl (2.07 g, 9.88 mmol) at 0° C. The mixture was stirred at room temperature for 12 h. After removal of solvent, the residue was dissolved in EtOAc (300 mL), washed with 5% $NaHO_3$ and brine, dried over $Na_2SO_4$. The solvent was removed and the residue was purified by silica gel flash chromatography to provide 55 as colorless oil (6.26 g, 65% yield). H NMR (d$_6$-DMSO) δ 8.10 (d, 1 H, J=8.0 Hz), 7.90-7.61 (m, 5 H), 7.49 (t, 1H, J=7.6 Hz), 7.42-7.21 (m, 8H), 6.90 (s, 1 H), 6.82 (d, 1H, J=8.8 Hz), 6.23 (d, 1H, J=2.9 Hz), 5.63 (m, 1H), 4.94-4.86 (m, 2H), 4.41 (m, 1H), 4.29 (dd, 1H, J=10.0 Hz & 12.5 Hz), 4.22-4.17 (m, 2H), 4.06 (dd, 1H, J=6.3 Hz & 14.3 Hz), 3.90 (dd, 1H, J=7.6 Hz & 14.4 Hz), 3.02 (m, 1H), 2.90 (m, 1H), 2.66 (dd, 1H, J=6.9 Hz & 15.4 Hz), 2.52 (dd, 1H, J=5.2 Hz & 15.2 Hz), 2.32 (s, 3H), 2.07 (m, 1H), 1.95-1.19 (m, 12H). FABMS (+Ve) m/z 690 [MH$^+$].

N-2-[(5-methylindolyl)methyl]pent-4-enyl(2S)-2-aminocyclohexyl)carbonylamino)]3-carbamoylpropanamide (56). To a solution of 55 (6.12 g, 8.87 mmol) in $CH_3CN$ (96 mL) was added piperidine (9.61 mL). The resulting solution was stirred at room temperature for 1.5 h. Evaporation provided a residue, which was purified by silica gel flash chromatography to provide 56 as colorless oil (3.52 g, 85%). H NMR (d$_6$-DMSO) δ 8.44 (s, 1H), 7.79 (m 1 H), 7.37-7.29 (m, 5H), 6.93 (m, 1H), 6.88 (s, 1 H), 6.30 (d, 1H, J=3.1 Hz), 5.73 (m, 1H), 5.04-4.98 (m, 2H), 4.44 (t, 1H, J=5.9 Hz), 4.08 (dd, 1H, J=7.7 Hz & 13.0 Hz), 3.95 (dd, 1H, J=7.5 Hz & 14.4 Hz), 3.10 (m, 1H), 2.96 (m, 1H) 2.54 (m, 1H), 2.43 (dd, 1H, J=6.1 Hz & 15.2 Hz), 2.36 (s, 3H), 2.12 (m, 1H), 1.98-1.84 (m, 2H), 1.79-1.12 (m, 10H). FABMS (+Ve) m/z 468 [MH$^+$].

Tert-butyl 3-[N-({N-[1-N-2-[(5-methylindolyl)methyl]pent-4-enyl carbamoyl)(1S)-2-carbamoylethyl]carbamoyl}cyclohexyl)carbamoyl)] (3S,4S)-4-(4-{[bis(tert-butoxy)carbonyl]methyl}phenyl)hept-6-enoate (58). To a solution of compound 56 (2.76 g, 5.91 mmol) and compound 57 (3.84 g, 7.68 mmol) in DMF (50 mL) was added HOAt (17.75 mL, 8.87 mmol) and EDCI.HCl (1.700 g, 8.87 mmol) at 0° C. The solution was stirred for at room temperature (1.5 h) then heated to 50° C. and stirred (24 h). The crude reaction mixture was evaporated in vacuo and residue was purified by silica gel flash chromatography to provide 58 as colorless oil (470 mg, 12% yield with recovered material 56 (762 mg). H NMR (d$_6$-DMSO) δ 8.21 (m, 1H), 7.40-7.12 (m, 10H), 6.93 (m, 1H), 6.83 (s, 1 H), 6.32 (dd, 1H, J=3.0 Hz & 8.6 Hz), 5.80-5.65 (m, 2H) 5.08-4.95 (m, 4H), 4.79 (m, 1H), 4.21-4.01 (m, 3H), 3.50 (m, 1H), 3.24 (m, 1H), 3.01-2.96 (m, 2H) 2.93 (d, 2H, J=21.2 Hz), 2.89 (m, 1H), 2.67-2.54 (m, 3H), 2.38 (s, 1.5H), 2.36 (s, 1.5H), 2.28-1.94 (m, 4H), 1.90-1.18 (m, 10H), 1.35 (s, 9H), 1.34 (s, 18H). FABMS (+Ve) m/z 946 [MH$^+$].

Tert-butyl 2-[(9S,10S,18S)-7,16,19-triaza-10-(4-{[bis(tert-butoxy) carbonyl]methyl}phenyl)-18-(carbamoylmethyl)-14-[(5-methylindolyl)methyl]-8,17,20-trioxospiro[5.14]icos-11-en-9-yl]acetate (60). To a solution of 58 (92 mg, 0.097 mmol) in $CH_2Cl_2$ (30 mL) was added ruthenium catalyst 17 (46 mg, 0.055 mmol) in $CH_2Cl_2$ (5 mL) under argon. The reaction mixture was stirred at 45° C. (48 h). The crude reaction mixture was then evaporated in vacuo, and residue was purified by silica gel flash chromatography to give 60 as yellow oil (44 mg, 49%). 11-(S): H NMR (CD$_3$OD) δ 7.36-7.12 (m, 10H), 7.01 (dd, 1H, J=1.4 Hz & 8.3 Hz), 5.87 (m, 1H), 5.56 (dd, 1H, J=10.1 Hz & 15.5 Hz), 4.57 (t, 1H, J=4.6 Hz), 4.25 (m, 1H), 4.07 (m, 1H), 3.99 (dd, 1H, J=10.0 Hz & 14.4 Hz), 3.83 (m, 1H), 3.28 (m, 1H), 3.05 (d, 2H, J=21.1 Hz), 3.04-2.99 (m, 3H), 2.71 (dd, 1H, J=12.0 Hz & 17.3 Hz), 2.55 (dd, 1H, J=5.0 Hz & 15.6 Hz), 2.42 (m, 1H), 2.38 (s, 3H), 2.15-1.92 (m, 2H), 1.87-1.29 (m, 10 H), 1.40 (s, 18H), 1.36 (s, 9H).

2-{(9S,10S,18S)-7,16,19-Triaza-18-(carbamoylmethyl)-14-[(5-methyl indolyl)methyl]-8,17,20-trioxo-10-[4-(phosphonomethyl)phenyl]spiro[5.14]icos-11-en-9-yl}acetic acid (61). A solution of 60 (14 mg, 0.0153 mmol) in a mixture of TFA-ethanedithol-$H_2O$ (2.0 mL, v:v, 3.8:0.1:0.1) was stirred at room temperature (1 h). The mixture was placed on rotavap and reduced in volume to 0.25 mL. Diethyl ether (5 mL) was added giving a purple solid. The solid was collected and purified by HPLC. Gradient condition: Started from 0.1% TFA in 5% $CH_3CN$/95% $H_2O$ solution to 0.1% TFA in 95% $CH_3CN$/5% $H_2O$ solution for 25 minutes, and continue 95% $CH_3CN$/5% $H_2O$ solution for additional 10 minutes; retention time is 28.549 min for analytical and 16.937 min for preparation. Lyophilization provided 61 as a pale solid (3.0 mg, 26% yield). It is a mixture of 5 and 62 (5:62=3:4). For 62: H NMR (d$_6$-DMSO) δ 8.44 (s, 1H), 8.35 (d, 1H, J=8.0 Hz), 7.64 (s, 1H), 7.38 (d, 1H, J=8.4 Hz), 7.31-7.15 (m, 7H), 6.94 (d, 1H, J=8.4 Hz), 6.30 (d, 1H, J=2.8 Hz), 5.81 (m, 1H), 5.63 (dd, 1H, J=9.6 Hz & 16.0 Hz), 4.31 (m, 1H), 4.19 (m, 1H), 4.06 (m, 1H), 3.73 (m, 1H), 3.43-3.20 (m, 2H), 2.91 (d, 2H, J=21.2 Hz), 2.84 (m, 1H), 2.68 (m, 1H), 2.41 (m, 1H), 2.35 (s, 3H), 2.31 (m, 1H), 2.04 (m, 3H), 1.88-1.74 (m, 4 H), 1.58-1.42 (m, 4H), 1.23-1.14 (m, 2H).

EXAMPLE 2

This example illustrates some of the properties of compounds in accordance with an embodiment of the invention.

Binding affinities were determined as follows. Surface Plasmon Resonance (SPR) Determination of Grb2 SH2 Domain-Binding Kd Values. Binding experiments were performed on a BIACORE S51 instrument (Biacore Inc., Piscataway N.J.). All Biotinylated Grb2 SH2 domain protein (b-Grb2) was expressed and purified (Protein Expression Laboratory and The Protein Chemistry Laboratory, SAIC—Frederick). The b-Grb2 was immobilized onto carboxymethyl 5' dextran surface (CM5 sensor chip, Biacore Inc.) by amine coupling. The lyophilized b-Grb2 was reconstituted in fifty percent DMSO in $H_2O$ to make a stock solution of 1 mg/mL and stored at −80° C. A 1:12.5 dilution of b-Grb2 was used for immobilization and prepared by dilution in acetate buffer pH-5.0, with 5% DMSO. 1×PBS (phosphate buffered saline, pH 7.4) was used as the running buffer.

An immobilization wizard was used to facilitate immobilization targeting. For b-Grb2, 2500-5000 resonance units (RU) of protein were captured on the CM5 sensor chip. Small molecule ligands were serially diluted in running buffer to concentrations of 1.25 nM-1500 nM, as described in each sensorgram and injected at 25° C. at a flow rate of 30 μl/min for 1 minute and dissociation was monitored for an additional 3 minutes. Surface regeneration was not used. Samples of differing concentrations of small molecule ligands were injected in increasing concentration, with every injection being performed in duplicate within each experiment. In order to subtract background noise from each data set, all samples were also run over an unmodified reference surface and injections of running buffer were performed throughout every experiment ("double referencing"). Up to six data sets were fit to a simple 1:1 interaction model or to a surface heterogeneity model ("complex model") for compound 41, using the global data analysis program CLAMP. Myszka, D. G.; Morton, T. A.; CLAMP: A biosensor kinetic data analysis program. *Trends Biochem. Sci.* 1998, 23, 149-150. The mean of the ratio and associated error were calculated according to known procedures. van Kempen, G. M.; van Vliet, L. J.; Mean and variance of ratio estimators used in fluorescence ratio imaging. *Cytometry* 2000, 39, 300-305.

ELISA-Based Determination of Grb2 SH2 Domain-Binding $IC_{50}$ Values. To multiwell plates pre-coated with streptavidin (SA) is added biotinylated Grb2 SH2 domain-MBP fusion protein. SH2 domain-fusion protein binds to the SA on the plate and unbound protein is then washed away and the plate is blocked using the commercial ELISA blocking agent, I-Block that contains detergent and casein (a milk protein). This blocking agent prevents subsequently-added constituents from sticking to the plastic well non-specifically. To the wells is then added horseradish peroxidase-(HRP)-SA-biotinylated-phosphopeptide as a pre-formed complex (termed "Complex"). [NOTE: The HRP-SA-biotinylated phosphopeptide complex is prepared ahead of time by combining a vast molar excess of SA-HRP with the biotinylated phosphopeptide to assure that all of the biotin sites are bound to SA-HRP before they are added to the well. This prevents those biotin sites from sticking to the SA coating on the plate, which would generate a signal even in the absence of biotinylated Grb2 SH2 domain-MBP fusion protein.] This complex binds to the Grb2 SH2 domain via the phosphopeptide. Unbound Complex is washed away before adding HRP substrate (OPD) to generate a color that is measured spectrophotometrically. Synthetic SH2 domain binding antagonists, at various concentrations, are added to wells in the presence of Complex to compete for HRP-SA-biotinylated-phosphopeptide binding to Grb2 SH2 domain protein. The intensity of the resulting color for each well as a function of the concentration of synthetic inhibitor added is recorded. Analysis of this data provides the $IC_{50}$ values indicated in Table 1.

TABLE 1

Grb2 SH2 Domain-Binding Affinities

| Compound No. | SPR Kd (nM) | ELISA $IC_{50}$ (nM) |
|---|---|---|
| 6 | 1.67 | — |
| 28 (as disodium salt) | 67 | 8.8 |
| 32 (as trisodium salt) | 3.62 | 3.3 |
| 33 (as disodium salt) | 1.65, 28.9 | 22.5 |
| 41 (as disodium salt) | 35.3 | 8.4 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of the formula:

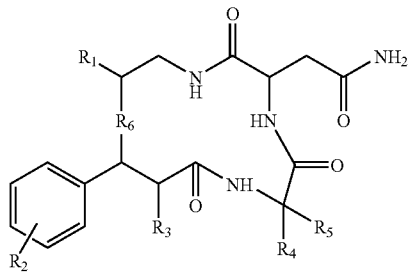

wherein $R_1$ is $C_6$-$C_{14}$ aryl heterocyclyl $C_1$-$C_6$ alkyl, whose aryl moiety is substituted with one or more groups selected from the group consisting of $C_1$-$C_6$ alkyl, halo, hydroxy, amino, $C_1$-$C_6$ alkoxy, and hydroxy $C_1$-$C_6$ alkyl;

$R_2$ is carboxy $C_1$-$C_6$ alkyl, carboxy $C_1$-$C_6$ alkylamino, oxalylamino, carboxy $C_1$-$C_6$ alkoxy, dicarboxy $C_1$-$C_6$ alkyl, dicarboxy $C_1$-$C_6$ alkyloxy, dicarboxyhalo $C_1$-$C_6$ alkyl, dicarboxyhalo $C_1$-$C_6$ alkyloxy, $RSO_2NH$- wherein R is $C_1$-$C_6$ alkyl, halo $C_1$-$C_6$ alkyl, $C_6$-$C_{14}$ aryl, $C_6$-$C_{14}$ aryl $C_1$-$C_6$ alkyl, or trifluoro $C_1$-$C_6$ alkyl, phosphono, phosphono $C_1$-$C_6$ alkyl, phosphonohalo $C_1$-$C_6$ alkyl, $C_6$-$C_{14}$ aryl $C_1$-$C_6$ alkyl phosphino $C_1$-$C_6$ alkyl, $C_1$-$C_6$ alkyl phosphino $C_1$-$C_6$ alkyl, phosphoryl, phosphoryl $C_1$-$C_6$ alkyl, phosphoryl $C_1$-$C_6$ alkoxy, $C_6$-$C_{14}$ aryl, or $C_6$-$C_{14}$ aryl $C_1$-$C_6$ alkyl, wherein the aryl and alkyl moieties are optionally substituted with a substituent selected from the group consisting of halo, hydroxy, carboxyl, amino, amino $C_1$-$C_6$ alkyl, $C_1$-$C_6$ alkyl, $C_1$-$C_6$ alkoxy, and keto;

$R_3$ is hydrogen, azido, amino, carboxy $C_1$-$C_6$ alkyl, $C_1$-$C_6$ alkoxycarbonyl $C_1$-$C_6$ alkyl, aminocarbonyl $C_1$-$C_6$ alkyl, or $C_1$-$C_6$ alkylcarbonylamino, wherein the alkyl portion of $R_3$ are optionally substituted with a substituent selected from the group consisting of halo, hydroxy, carboxyl, amino, amino $C_1$-$C_6$ alkyl, $C_1$-$C_6$ alkyl, $C_1$-$C_6$ alkoxy, and keto;

$R_4$ and $R_5$, are independently selected from the group consisting of hydrogen, $C_1$-$C_6$ alkyl, $C_3$-$C_8$ cycloalkyl, and heterocyclyl, or $R_4$ and $R_5$ together form a $C_3$-$C_8$ cycloalkyl or heterocyclyl; and $R_6$ is a linker;

said heterocyclyl is a 4-7 membered ring comprising at least one hetero atom selected from the group consisting of O, N, and S;

or a pharmaceutically acceptable salt thereof.

2. The compound or pharmaceutically acceptable salt of claim 1, wherein $R_1$ is $C_6$-$C_{14}$ aryl heterocyclyl $C_1$-$C_6$ alkyl, whose aryl moiety is substituted with $C_1$-$C_6$ alkyl.

3. The compound or pharmaceutically acceptable salt of claim 2, wherein $R_1$ is a phenyl heterocyclyl $C_1$-$C_6$ alkyl whose aryl moiety is substituted with $C_1$-$C_6$ alkyl.

4. The compound or pharmaceutically acceptable salt of claim 3, wherein $R_1$ is a phenyl heterocyclyl methyl whose aryl moiety is substituted with $C_1$-$C_6$ alkyl.

5. The compound or pharmaceutically acceptable salt of claim 4, wherein $R_1$ is methyl indolyl methyl.

6. The compound or pharmaceutically acceptable salt of claim 1, wherein $R_2$ is carboxy $C_1$-$C_6$ alkyl, oxalylamino, dicarboxy $C_1$-$C_6$ alkyl, $RSO_2NH$—wherein R is $C_1$-$C_6$ alkyl, halo $C_1$-$C_6$ alkyl, $C_6$-$C_{14}$ aryl, $C_6$-$C_{14}$ aryl $C_1$-$C_6$ alkyl, or trifluoro $C_1$-$C_6$ alkyl, phosphono $C_1$-$C_6$ alkyl, phosphonohalo $C_1$-$C_6$ alkyl, $C_6$-$C_{14}$ aryl $C_1$-$C_6$ alkyl phosphino $C_1$-$C_6$ alkyl, $C_1$-$C_6$ alkyl phosphino $C_1$-$C_6$ alkyl, $C_6$-$C_{14}$ aryl, or $C_6$-$C_{14}$ aryl $C_1$-$C_6$ alkyl, wherein the aryl and alkyl moieties are optionally substituted with a substituent selected from the group consisting of halo, hydroxy, carboxyl, amino, amino $C_1$-$C_6$ alkyl, $C_1$-$C_6$ alkyl, $C_1$-$C_6$ alkoxy, and keto.

7. The compound or pharmaceutically acceptable salt of claim 6, wherein $R_2$ is carboxy $C_1$-$C_6$ alkyl, oxalylamino, dicarboxy $C_1$-$C_6$ alkyl, $RSO_2NH$—wherein R is $C_1$-$C_6$ alkyl, halo $C_1$-$C_6$ alkyl, $C_6$-$C_{14}$ aryl, $C_6$-$C_{14}$ aryl $C_1$-$C_6$ alkyl, or trifluoro $C_1$-$C_6$ alkyl, phosphono $C_1$-$C_6$ alkyl, phosphonohalo $C_1$-$C_6$ alkyl, $C_6$-$C_{14}$ aryl $C_1$-$C_6$ alkyl phosphino $C_1$-$C_6$ alkyl, or $C_1$-$C_6$ alkyl phosphino $C_1$-$C_6$ alkyl.

8. The compound or pharmaceutically acceptable salt of claim 7, wherein $R_2$ is carboxy methyl, oxalylamino, dicarboxy methyl, phosphono methyl, benzyl phosphino methyl, or methyl phosphinomethyl.

9. The compound or pharmaceutically acceptable salt of claim 1, wherein $R_3$ is carboxy $C_1$-$C_6$ alkyl, wherein the alkyl portion is optionally substituted with a substituent selected from the group consisting of halo, hydroxy, carboxyl, amino, amino $C_1$-$C_6$ alkyl, $C_1$-$C_6$ alkyl, $C_1$-$C_6$ alkoxy, and keto.

10. The compound or pharmaceutically acceptable salt of claim 9, wherein $R_3$ is carboxy $C_1$-$C_6$ alkyl, wherein the alkyl portion is optionally substituted with hydroxy.

11. The compound or pharmaceutically acceptable salt of claim 10, wherein $R_3$ is carboxy methyl or carboxy hydroxymethyl.

12. The compound or pharmaceutically acceptable salt of claim 1, wherein $R_4$ and $R_5$ together form a $C_3$-$C_8$ cycloalkyl.

13. The compound or pharmaceutically acceptable salt of claim 12, wherein $R_4$ and $R_5$ together form cyclohexyl.

14. The compound or pharmaceutically acceptable salt of claim 1, wherein $R_6$ is a $C_2$-$C_4$ alkylenyl, $C_2$-$C_4$ alkenylenyl, or $C_2$-$C_4$ alkynylenyl, which is optionally substituted.

15. The compound or pharmaceutically acceptable salt of claim 14, wherein $R_6$ is a $C_2$-$C_4$ alkenylenyl.

16. The compound or pharmaceutically acceptable salt of claim 15, wherein $R_6$ is $C_3$ alkenylenyl.

17. The compound of claim 1, which is

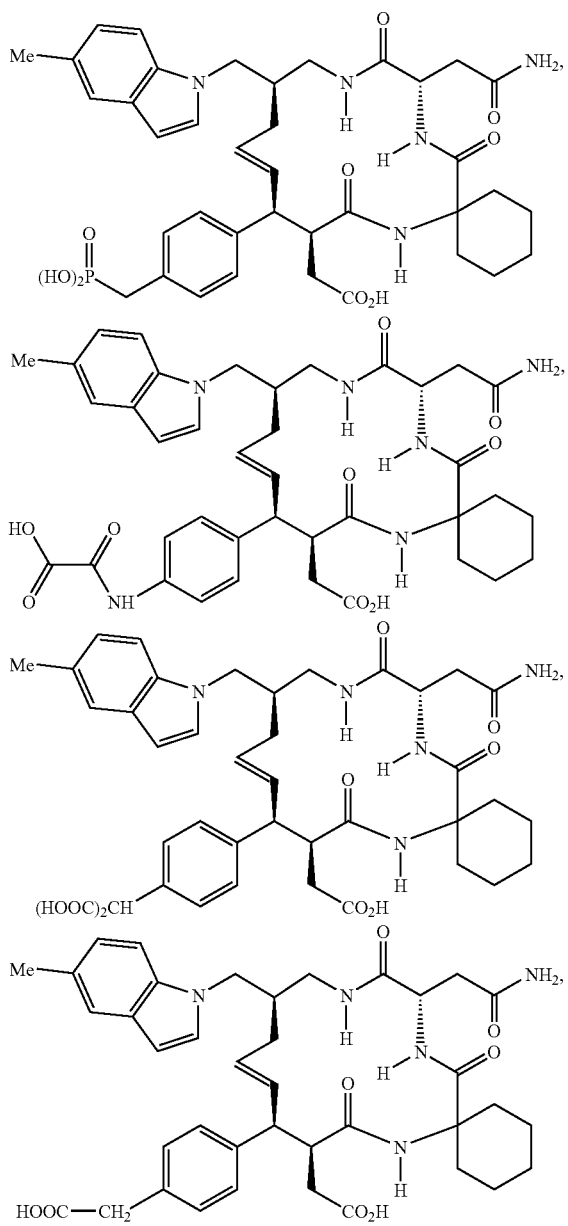

-continued

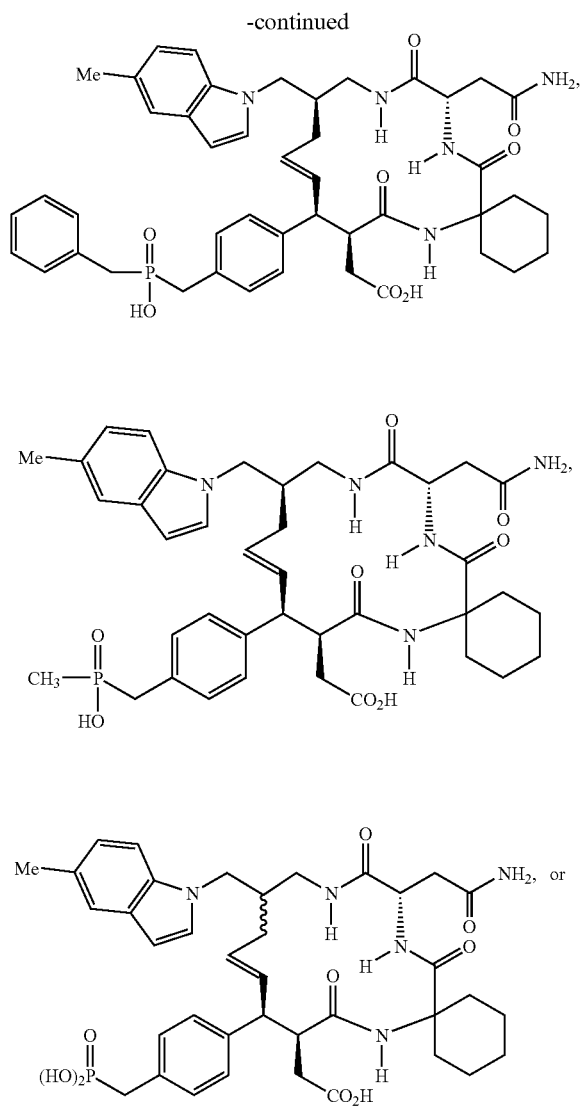

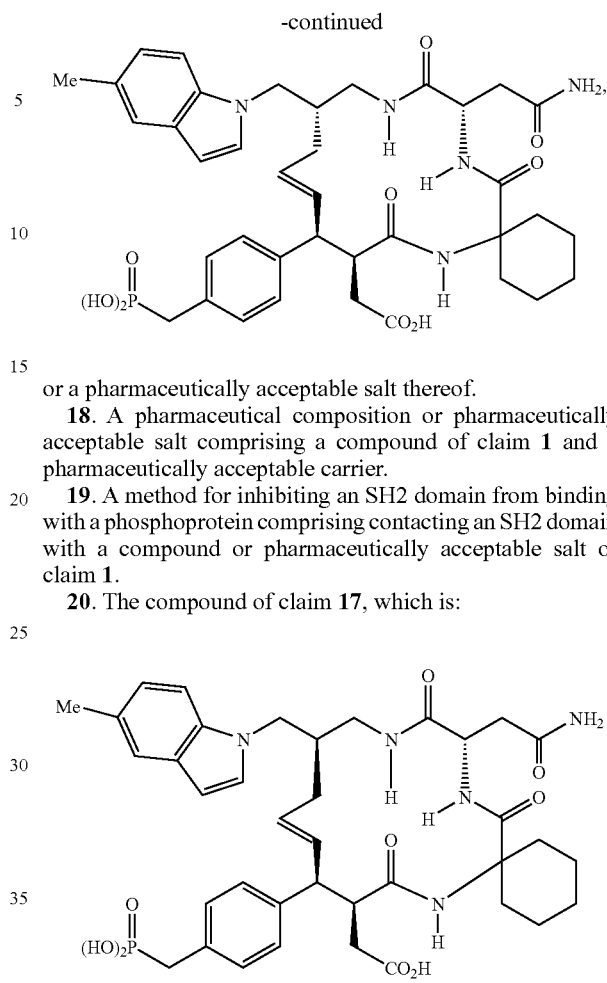

or a pharmaceutically acceptable salt thereof.

18. A pharmaceutical composition or pharmaceutically acceptable salt comprising a compound of claim 1 and a pharmaceutically acceptable carrier.

19. A method for inhibiting an SH2 domain from binding with a phosphoprotein comprising contacting an SH2 domain with a compound or pharmaceutically acceptable salt of claim 1.

20. The compound of claim 17, which is:

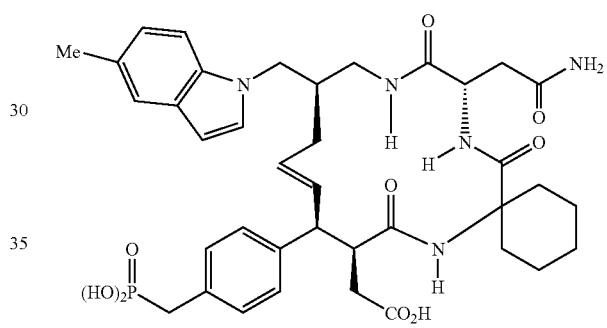

or a pharmaceutically acceptable salt thereof.

21. A pharmaceutical composition comprising the compound or salt of claim 20.

* * * * *